(12) United States Patent
Lin et al.

(10) Patent No.: US 9,175,062 B2
(45) Date of Patent: Nov. 3, 2015

(54) HUMAN SOLUBLE RECEPTOR FOR ADVANCED GLYCATION END PRODUCTS (SRAGE), METHODS OF PREPARING HUMAN SRAGE, AND TREATMENT METHODS USING SRAGE

(71) Applicant: The United States of America, as represented by the Secretary, Department of Health and Human Services, Washington, DC (US)

(72) Inventors: Li Lin, Baltimore, MD (US); Sungha Park, Seoul (KR); Wen Wei, Cockeysville, MD (US); Rui-Ping Xiao, Baltimore, MD (US); Mark I. Talan, Baltimore, MD (US); Edward G. Lakatta, Bel Air, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/368,374

(22) PCT Filed: Jan. 3, 2013

(86) PCT No.: PCT/US2013/020103
§ 371 (c)(1),
(2) Date: Jun. 24, 2014

(87) PCT Pub. No.: WO2013/103688
PCT Pub. Date: Jul. 11, 2013

(65) Prior Publication Data
US 2015/0051136 A1 Feb. 19, 2015

Related U.S. Application Data

(60) Provisional application No. 61/582,574, filed on Jan. 3, 2012.

(51) Int. Cl.
*C07K 14/705* (2006.01)
*A61K 38/17* (2006.01)

(52) U.S. Cl.
CPC ......... *C07K 14/70503* (2013.01); *A61K 38/177* (2013.01); *C07K 14/705* (2013.01)

(58) Field of Classification Search
CPC ........... C07K 14/705; C07K 14/70503; A61K 38/177
See application file for complete search history.

(56) References Cited

U.S. PATENT DOCUMENTS

| 2005/0129682 | A1* | 6/2005 | Schmidt et al. | 424/143.1 |
| 2007/0099829 | A1* | 5/2007 | Stern et al. | 514/12 |
| 2009/0060925 | A1 | 3/2009 | Mjalli et al. | |
| 2009/0228997 | A1* | 9/2009 | Schmidt et al. | 800/14 |

OTHER PUBLICATIONS

Yamagishi et al., 2010, Soluble form of a receptor for advanced glycation end products (sRAGE) as a biomarker, Frontiers in Bioscience, E2: 1184-1195.*
Nin et al., 2010, Higher Plasma Soluble Receptor for Advanced Glycation End Products (sRAGE) Levels are Associated with Incident Cardiovascular Disease and All-Cause Mortality in Type 1 Diabetes, Diabetes, 59: 2027-2032.*
Thomas et al., 2011, Soluble receptor for AGE (RAGE) is a novel independent predictor of all-cause and cardiovascular mortality in type 1 diabetes, Diabetologia, 54: 2669-2677.*
Colhoun et al., 2011, Total Soluble and Endogenous Secretory Receptor for Advanced Glycation End products as predictive Biomarkers of Coronary Heart Disease Risk in Patients with Type 2 Diabetes, Diabetes, 60: 2379-2385.*
Kim et al., 2012, Plasma levels of soluble receptor for advanced glycation end products (sRAGE) and proinflammatory ligand for RAGE (EN-RAGE) are associated with carotid atherosclerosis in patients with peritoneal dialysis, Atherosclerosis, 220: 208-214.*
Ding et al., 2005, Splice variants of the receptor for advanced glycosylation end products (RAGE) in human brain, Neuroscience Letters, 373: 67-72.*
Park et al., 2011, The G82S Polymorphism Promotes Glycosylation of the Receptor for Advanced Glycation End Products (RAGE) at Asparagine 81, The Journal of Biological Chemistry, 286(24): 21384-21392.*
Englert et al, "Large Scale Isolation and Purification of Soluble RAGE from Lung Tissue," *Protein Expression and Purification*, vol. 61:99-101, 2008.
Park et al., "The G82S Polymorphism Promotes Glycosylation of the Receptor for Advanced Glycation End Products (RAGE) at Asparagine 81: Comparison of Wild-Type Rage with the G82S Polymorphic Variant," *J. Biol. Chem.*, vol. 286:21384-21392, 2011.
Sparvero et al., "RAGE (Receptor for Advanced Glycation Endproducts), RAGE Ligands, and their Role in Cancer and Inflammation," *J. Translational Med.*, vol. 7:17-38, 2009.
Srikrishna et al., "N-Glycans on the Receptor for Advanced Glycation End Products Influence Amphoterin Binding and Neurite Outgrowth," *J. Neurochem.*, vol. 80:998-1008, 2002.
Srikrishna et al., "Carboxylated N-glycans on RAGE Promote S100A12 Binding and Signaling," *J. Cell Biochem.*, vol. 111:645-659, 2010.
Yonekura et al., "Novel Splice Variants of the Receptor for Advanced Glycation End-Products Expressed in Human Vascular Endothelial Cells and Pericytes, and their Putative Roles in Diabetes-Induced Vascular Injury," *Biochem. J.*, vol. 370:1097-1109, 2003.

* cited by examiner

*Primary Examiner* — Amber D Steele
(74) *Attorney, Agent, or Firm* — Klarquist Sparkman, LLP

(57) ABSTRACT

The present disclosure provides a method for recombinant production of human sRAGE in mammalian cells, as well as a human sRAGE having a mammalian post-translational modification and compositions thereof. The present disclosure also provides a method of treating a vascular disease, injury, or inflammation in a mammal by administering to a mammal with a vascular disease, injury, or inflammation a composition comprising human sRAGE having a mammalian post-translational modification, thereby treating the vascular disease, injury, or inflammation in the mammal.

12 Claims, 30 Drawing Sheets

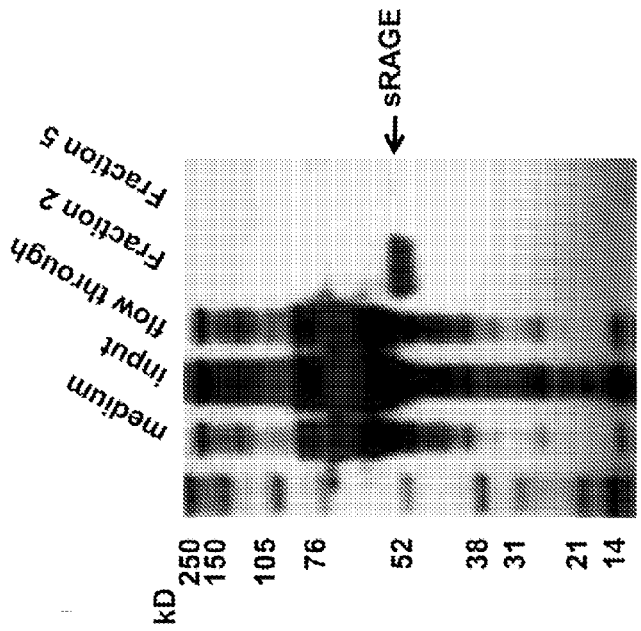
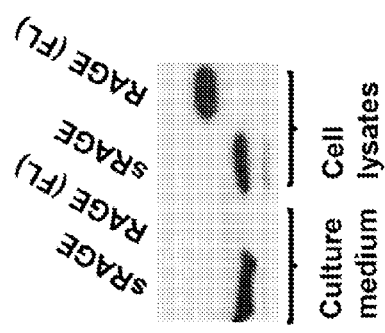
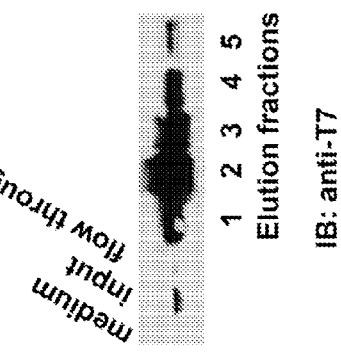

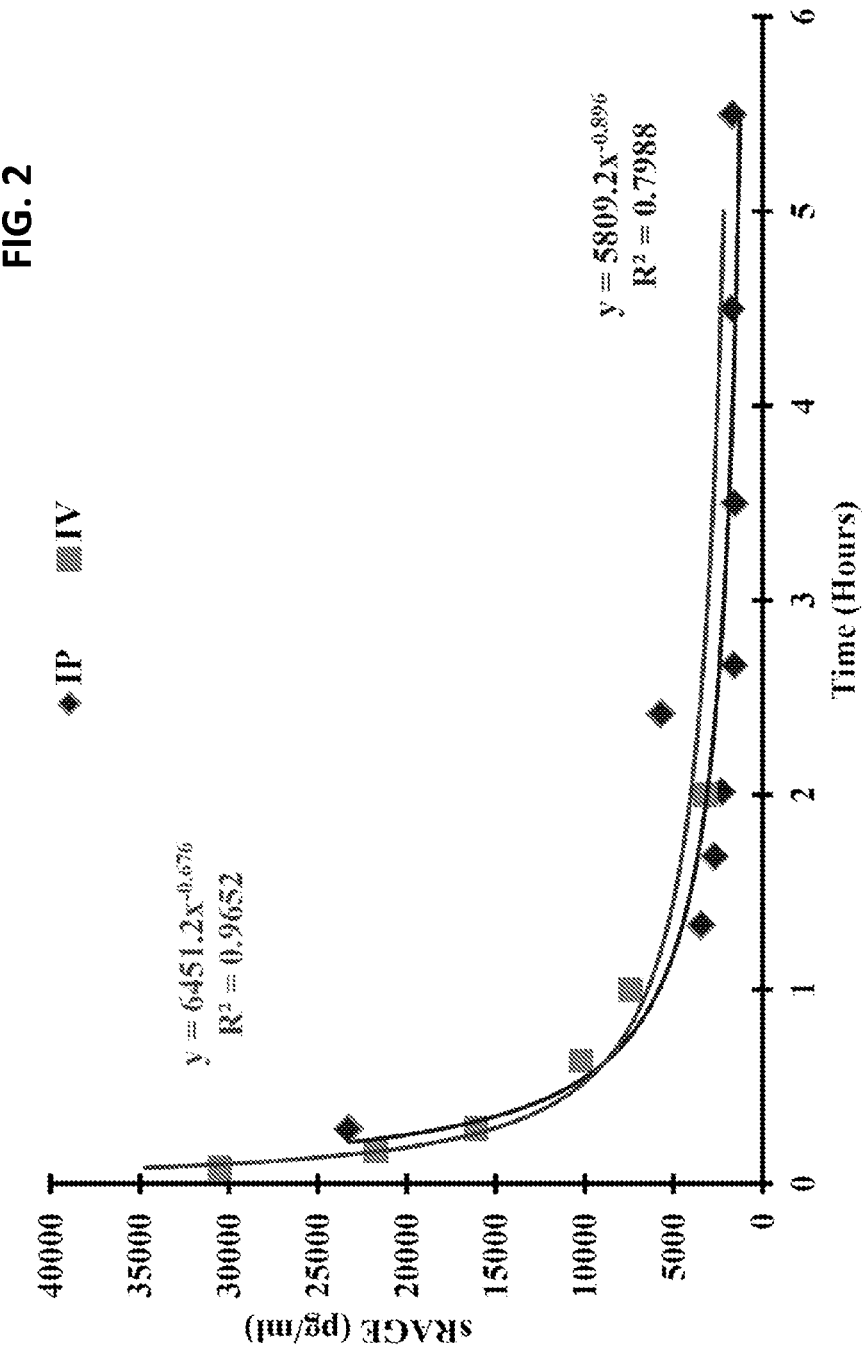

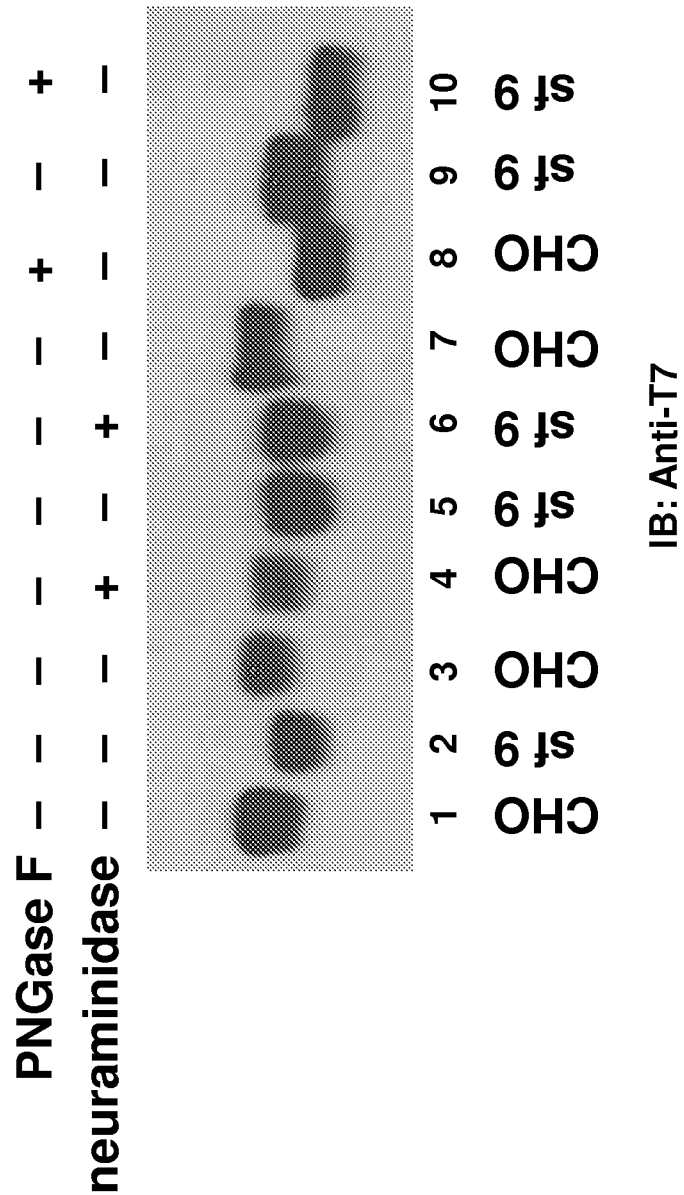

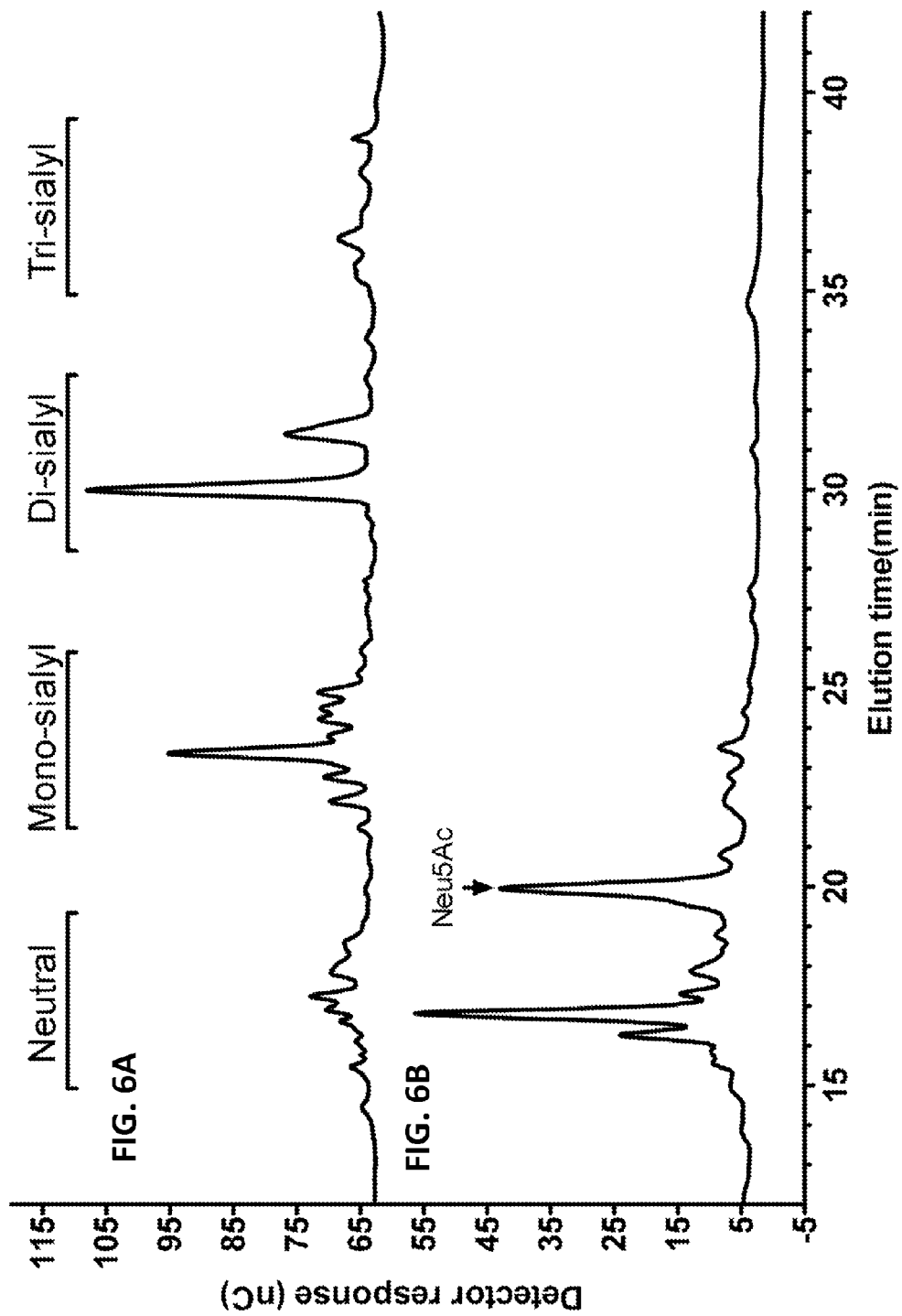

Lumen Diameter

Wall Thickness

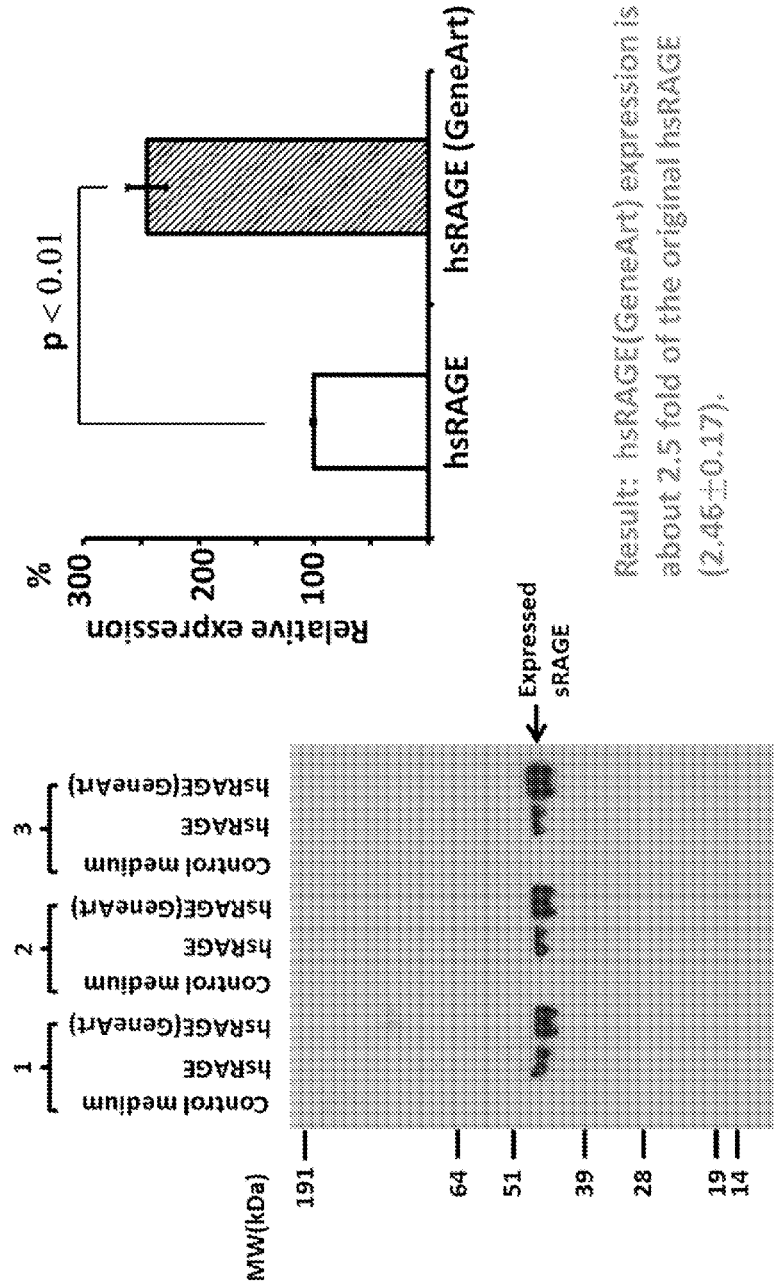

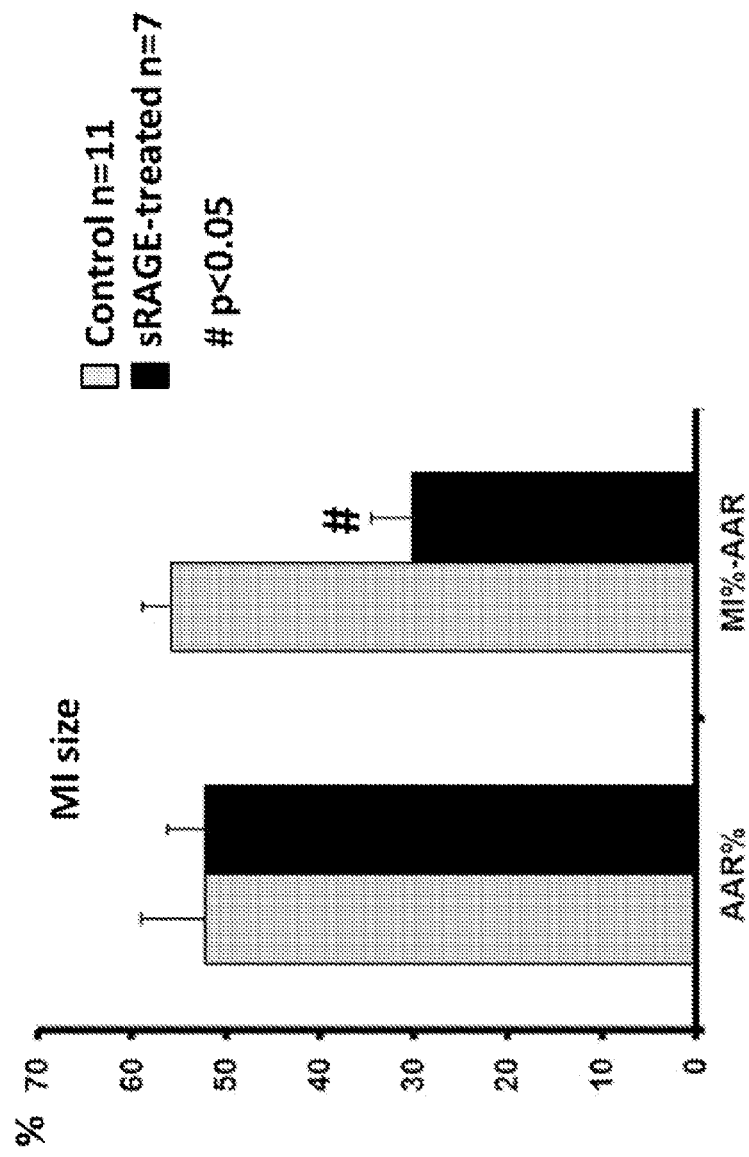

HUMAN SOLUBLE RECEPTOR FOR ADVANCED GLYCATION END PRODUCTS (SRAGE), METHODS OF PREPARING HUMAN SRAGE, AND TREATMENT METHODS USING SRAGE

CROSS REFERENCE TO RELATED APPLICATIONS

This is the U.S. National Stage of International Application No. PCT/US2013/020103, filed Jan. 3, 2013, published in English under PCT Article 21(2), which claims the benefit of U.S. Provisional Application No. 61/582,574, filed Jan. 3, 2012, which is herein incorporated by reference in its entirety.

FIELD

The present disclosure concerns production of soluble receptor for advanced glycation end products (sRAGE) in mammalian cells and the use of sRAGE having mammalian post-translational modifications for the treatment of vascular diseases and disorders.

BACKGROUND

Arterial restenosis is a serious pathological complication that can follow surgical cardiovascular interventions such as angioplasty. The receptor for advanced glycation end products (RAGE) is a protein implicated in the development of vascular hyperplasia and in atherogenesis. A soluble form of RAGE, designated sRAGE, is used as a therapeutic agent that is believed to act as a decoy to diminish RAGE-dependent signaling, thereby attenuating inflammation and pathogenic consequences. RAGE is a multi-ligand receptor which interacts with advanced glycosylation end products (AGE), and with other molecules implicated in homeostasis, development, inflammation, and certain diseases, such as diabetes and Alzheimer's disease. sRAGE also has been associated with anti-mitotic effects. The administration of sRAGE has been used to treat arterial restenosis and atherosclerosis in animal models.

There is a need for improved methods of preparing sRAGE, as well as a need for sRAGE having an increased potency and a lower therapeutically effective dose.

SUMMARY

Provided herein is a method of treating a mammal having a vascular disease, injury, or inflammation by administering to the mammal a sRAGE polypeptide comprising a mammalian post-translation modification, such as mammalian glycosylation. In some embodiments, the sRAGE polypeptide is administered at a significantly lower dose (e.g. 1000-fold lower dose) than sRAGE produced in non-mammalian cells (such as insect cells). In some examples, the sRAGE polypeptide is administered at a dose that does not exceed about 6 ng/g body weight of the mammal. In non-limiting examples, the amino acid sequence of the sRAGE polypeptide is at least 85% identical to amino acid residues 23-340 of SEQ ID NO: 1, or at least 85% identical to SEQ ID NO: 4, SEQ ID NO: 10 or SEQ ID NO: 11.

The present disclosure further provides a method for the production of human sRAGE in mammalian cells, which human sRAGE displays high potency and allows for use of a decreased dose as compared to sRAGE produced through expression in non-mammalian cells. In some embodiments, the present disclosure provides a method of producing a human sRAGE polypeptide in mammalian cells by (a) providing an expression vector comprising a nucleic acid sequence encoding the human sRAGE polypeptide; (b) establishing a mammalian cell with the expression vector in a medium and under conditions in which the nucleic acid sequence is expressed and the human sRAGE polypeptide is produced; and (c) isolating or purifying the human sRAGE from the medium, wherein the sRAGE polypeptide comprises a mammalian post-translational modification. In some examples, the nucleic acid molecule encoding the human sRAGE polypeptide is codon-optimized for expression in a particular cell type. The nucleic acid molecule is optionally further optimized for mRNA structure that enhances translation, for example by removing a hairpin structure.

Also provided is a nucleic acid molecule encoding a human sRAGE polypeptide, the sequence of which is codon-optimized for expression in *Cricetulus griseus* (Chinese hamster) cells, such as Chinese hamster ovary (CHO) cells. In some embodiments, the sequence of the nucleic acid molecule is at least 85% identical to SEQ ID NO: 12. Further provided are vectors comprising the codon-optimized nucleic acid molecule and isolated host cells comprising the vectors.

The present disclosure also provides an isolated or purified human sRAGE polypeptide having a mammalian post-translational modification, as well as compositions comprising a human sRAGE polypeptide having a mammalian post-translational modification.

The foregoing and other features and advantages will become more apparent from the following detailed description of several embodiments, which proceeds with reference to the accompanying figures.

BRIEF DESCRIPTION OF THE DRAWINGS

FIG. 1A depicts expression of sRAGE and full-length (FL) RAGE following transient expression in CHO cells by immunoblotting (IB). FIG. 1B depicts the presence of sRAGE in various fractions from a T7 affinity purification procedure by IB. FIG. 1C is an image of a Silver stained SDS-PAGE gel containing the indicated fractions from a T7 affinity purification procedure.

FIG. 2 is a graph depicting human sRAGE concentration produced in mammalian cells after intraperitoneal (IP) injection as compared to intravenous (IV) injection in rat serum samples at 0-6 hours following administration of a single bolus of 7 ng/g sRAGE. Concentration was determined by ELISA.

FIG. 5 is an immunoblot demonstrating that the N-glycan structures of sRAGE$^{CHO}$ and sRAGE$^{sf9}$ are different. Cell culture media of transfected CHO or sf9 (10 μg) were collected and resolved on SDS 4-12% PAGE. Immunoblots were performed using anti-T7 antibody. Lanes 1-2: untreated media; lanes 3-6: neuraminidase and mock-treated media; lanes 7-10: PNGase F and mock-treated media.

FIGS. 6A-6B are chromatograms of the sialic acid profiles of the N-glycan from purified recombinant human sRAGE expressed in CHO cells before (FIG. 6A) and after (FIG. 6B) desialylation by acid treatment.

(FIGS. 7A-7D) Sensorgrams of HMGB1 (analyte concentrations used in the study were 31.25, 62.5, 125, 250 and 500 nM). (FIG. 7A) sRAGE$^{CHO}$; (FIG. 7B) sRAGE$^{CHO}$(desialylated); (FIG. 7C) sRAGE$^{sf9}$; (FIG. 7D) sRAGE$^{CHO}$(N25T/N81T). (FIGS. 7E-7H) Sensorgrams of S100B (analyte concentrations used in the study were 12.5, 25, 50, 100 and 200 nM). The insets show steady state binding curves with Y axis as response units (RU) and X axis as concentration (nM). (FIG. 7E) sRAGE$^{CHO}$; (FIG. 7F) sRAGE$^{CHO}$(desialylated); (FIG. 7G) sRAGE$^{sf9}$; (FIG. 7H) sRAGE$^{CHO}$ (N25T/N81T).

(FIG. 8A) HMGB1-stimulated; (FIG. 8B) S100B-stimulated. *: $p<0.05$; : $p<0.01$; *: $p<0.0001$.

(FIG. 9A) Inhibition of HMGB-induced NF-κB activation by sRAGEs. (FIG. 9B) Inhibition of S100B-induced NF-κB activation by sRAGEs. *: $p<0.05$; : $p<0.01$; *: $p<0.0001$.

(FIG. 10A) Linear regression of lumen diameter measured with histology (Y axis) and sonography (X axis). (FIG. 10B) Linear regression of wall thickness measured with histology (Y axis) and sonography (X axis).

(FIG. 11A) Histomorphological analyses of carotid artery sections of rats. Both percentage of the intima area in the vessel wall (left), and the intima/media ratio (I/M, right) were measured. NS: statistically not significant; error bars represent standard error of the mean (SEM) ($p<0.05$). (FIG. 11B) Carotid artery lumen diameter and wall thickness measured with sonography. Rats in different treatment groups were monitored with vessel sonography at the day of balloon injury, 1, and 2 weeks after the injury. The measured parameters clearly differentiate at 2-week post-injury.

(FIG. 16A) The percentage of neointima area in the vessel wall. (FIG. 16B) The I/M ratio of the vessels. NS: not significant. (FIG. 16C-16H) Representative histological vessel sections from each treatment group: (FIG. 16C) Non-operated; (FIG. 16D) sRAGE$^{CHO}$-treated; (FIG. 16E) sRAGE$^{CHO}$(desialylated)-treated; (FIG. 16F) sRAGE$^{sf9}$-treated; (FIG. 16G) sRAGE$^{CHO}$(N25T/N81T)-treated; (FIG. 16H) placebo. Paired arrows mark neointima areas.

FIG. 18 shows hsRAGE expression is enhanced by Gene-Art re-engineering. The left panel shows human sRAGE expression from 3 sets of cells independently-transfected with either the original (native cDNA) or GeneArt-reengineered sRAGE cDNA. A total of 10 μg of collected medium was resolved with SDS-PAGE and blotted with anti-T7 antibodies. Cell culture medium from untransfected CHO cells was used as a negative control. The right panel shows the average fold increase in expression of sRAGE (GeneArt) relative to the original sRAGE cDNA, measured with densitometry.

FIG. 19 is a graph showing sRAGE$^{CHO}$ blocks acute ischemic myocardial infarction in a rat acute coronary artery ligation model. Rates were injected i.p. with sRAGE$^{CHO}$ (1 μg/kg) immediately after left coronary artery ligation. Myocardial infarction (MI) size was assessed 24 hours after ligation by Evans Blue and TIC (2,3,5-triphenyltetrazolium chloride) staining. The percentage of AAR (area at risk), and MI within the AAR were assessed.

SEQUENCE LISTING

Figure 3:
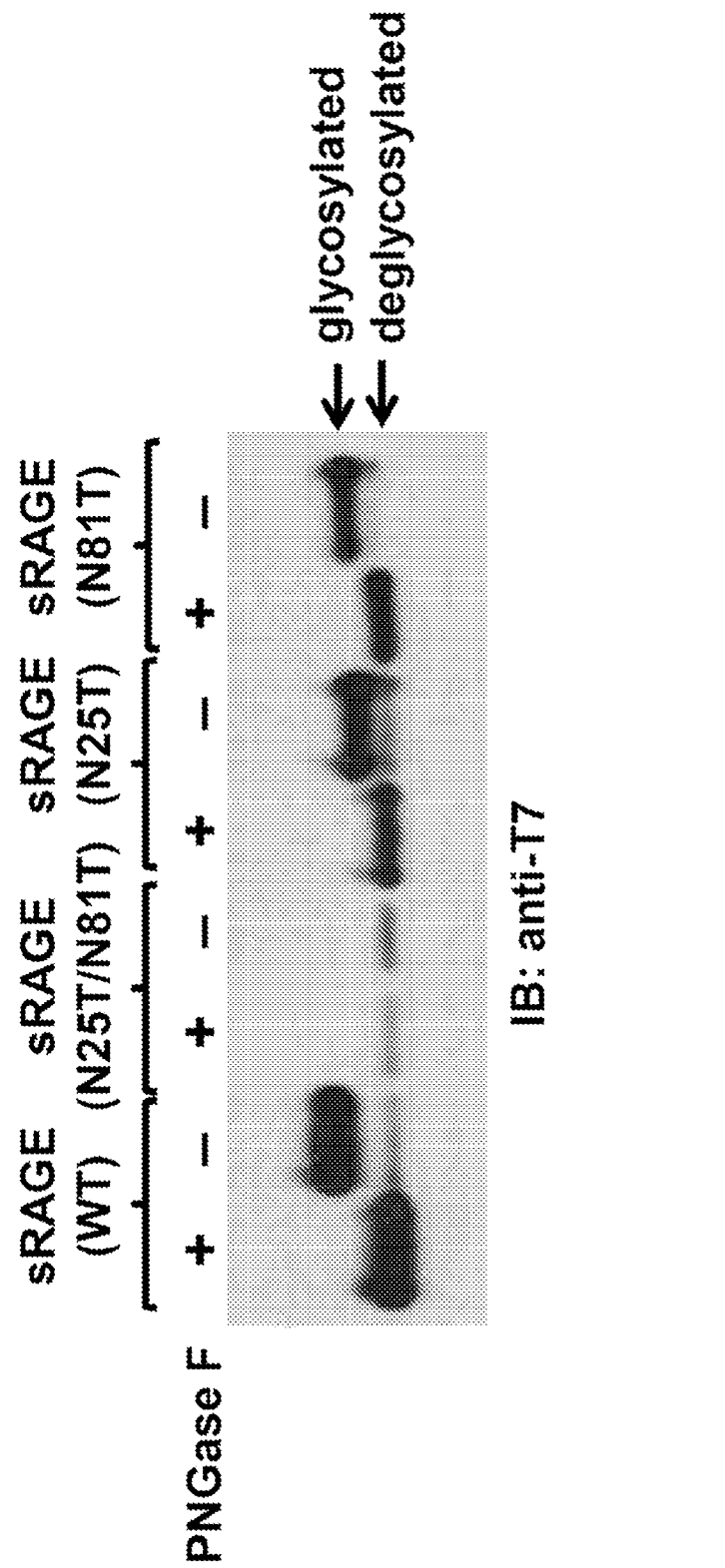
FIG. 3 is an immunoblot of glycosylated and unglycosylated sRAGE in culture medium following transient expression in CHO cells of wild-type (WT) sRAGE, sRAGE (N25T/N81T), sRAGE (N25T), or sRAGE (N81T), before and after treatment with peptide-N-glycosidase F (PNGase F).

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on May 23, 2014, 21.6 KB, which is incorporated by reference herein. In the accompanying Sequence Listing:

SEQ ID NO: 1 is the amino acid sequence of human advanced glycosylation end product-specific receptor (RAGE) (GenBank™ Accession No. NP_001127.1).

SEQ ID NO: 2 is the nucleotide sequence of an expression module encoding human T7-sRAGE fusion protein.

SEQ ID NO: 3 is the amino acid sequence of the T7 epitope tag.

SEQ ID NO: 4 is the amino acid sequence of a human T7-sRAGE fusion protein.

SEQ ID NO: 5 is the nucleotide sequence of the N25T forward primer.

SEQ ID NO: 6 is the nucleotide sequence of the N25T reverse primer.

SEQ ID NO: 7 is the nucleotide sequence of the N81T forward primer.

SEQ ID NO: 8 is the nucleotide sequence of the N81T reverse primer.

SEQ ID NO: 9 is the nucleotide sequence of a cDNA encoding T7-sRAGE with a thrombin cleavage site.

SEQ ID NO: 10 is the amino acid sequence of T7-sRAGE with a thrombin cleavage site.

SEQ ID NO: 11 is the amino acid sequence of sRAGE with a polyGly linker at the N-terminus (after thrombin cleavage).

SEQ ID NO: 12 is the nucleotide sequence of a codon-optimized (for *Cricetulus griseus*) and translation optimized T7-sRAGE.

DETAILED DESCRIPTION

I. Abbreviations

BSA bovine serum albumin
CHO Chinese hamster ovary
ELISA enzyme-linked immunosorbent assay
FL full length
Fuc fucose
Gal galactose
GlcNAc N-acetylglucosamine
H&E hematoxylin and eosin
HPAEC high-performance anion-exchange chromatography
hsRAGE human soluble RAGE
I/M intima/media ratio
IB immunoblot
ICAM-1 intracellular adhesion molecule-1
Man 3-mannose
NBF neutral buffered formalin
Neu5AC N-acetylneuraminic acid
PBS phosphate buffered saline
PNGase peptide-N-glycosidase F
RAGE receptor for advanced glycation end products
SDS-PAGE sodium dodecyl sulfate polyacrylamide gel electrophoresis
sRAGE soluble receptor for advanced glycation end products
SPR surface plasmon resonance
TFA trifluoroacetic acid
VCAM-1 vascular cell adhesion molecule-1

II. Terms and Methods

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Administration: The introduction of a composition into a subject by a chosen route. For example, if the chosen route is intravenous, the composition is administered by introducing the composition into a vein of the subject. Exemplary routes of administration include, but are not limited to, injection (such as subcutaneous, intramuscular, intradermal, intraperitoneal, and intravenous), oral, intraductal, sublingual, rectal, transdermal, intranasal, vaginal and inhalation routes.

Codon: A series of three nucleotides that encodes a specific amino acid. There are 64 different codons (61 codons for encoding amino acids, and 3 stop codons), but only 20 different translated amino acids. Thus, many amino acids are encoded by more than one codon. Different species often have a particular preference for a specific codon that encodes an amino acid (often referred to as codon usage bias).

Codon-optimized: A "codon-optimized" nucleic acid refers to a nucleic acid sequence that has been altered such that the codons are optimal for expression in a particular system (such as a particular species or group of species). For example, a nucleic acid sequence can be optimized for expression in mammalian cells, or expression in a particular species of mammal. Codon optimization does not alter the amino acid sequence of the encoded protein.

Glycosylation: The process by which sugar moieties are chemically attached to proteins. N-linked glycosylation specifically refers to the attachment of sugar molecules to a nitrogen atom in an amino acid residue of a protein. There are three major classes of N-linked saccharides—high-mannose oligosaccharides, complex oligosaccharides and hybrid oligosaccharides. O-linked glycosylation refers to the attachment of a sugar molecule to an oxygen atom in an amino acid residue of a protein.

Isolated: An "isolated" biological component (such as a nucleic acid molecule or protein) has been substantially separated or purified away from other biological components of the cell or organism in which the component naturally occurs, such as other chromosomal and extra-chromosomal DNA and RNA, or proteins. Nucleic acids and proteins that have been "isolated" include nucleic acids and proteins purified by standard purification methods. The term also embraces nucleic acids and proteins prepared by recombinant expression in a host cell, as well as chemically synthesized nucleic acids or proteins, or fragments or variants thereof.

Mammal: This term includes both human and non-human mammals.

N-glycan profile: Refers to the composition of N-glycosylation present in a protein.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced.

The term "residue" or "amino acid residue" includes reference to an amino acid that is incorporated into a protein, polypeptide, or peptide.

Conservative amino acid substitutions are those substitutions that, when made, least interfere with the properties of the original protein, that is, the structure and especially the function of the protein is conserved and not significantly changed by such substitutions. Examples of conservative substitutions are shown below.

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Post-translational modification: A chemical modification of a protein that occurs after it is translated. Post-translational modifications can alter the function or activity of the protein by attaching other biochemical functional groups (e.g. acetate, phosphate, lipids or carbohydrates), change the chemical nature of the protein and/or change the structure of the protein (e.g. disulfide bonds). As used herein a "mammalian post-translation modification" includes any post-translational modification that is specific to mammalian cells (as opposed to cells from other types of organisms, such as insects). In some embodiments of the present disclosure, the mammalian post-translation modification comprises mammalian glycosylation, mammalian phosphorylation, mammalian sulfation, mammalian carboxylation, mammalian hydroxylation, mammalian acetylation, mammalian myristoylation, mammalian farnesylation, mammalian ADP ribosylation, mammalian disulfide formation, mammalian SUMOylation, or any combination thereof. In specific examples, the mammalian post-translation modification comprises mammalian-specific glycosylation. For a review of mammalian post-translational modifications see, for example, Walsh and Jefferis, *Nat Biotech* 24:1241-1252, 2006.

Purified: The term "purified" does not require absolute purity; rather, it is intended as a relative term. Thus, for example, a purified polypeptide, protein or other active compound is one that is isolated in whole or in part from naturally associated proteins and other contaminants, in which the polypeptide, protein or other active compound is purified to a measurable degree relative to its naturally occurring state, for example, relative to its purity within a cell extract or chemical synthesis checker. In certain embodiments, the term "substantially purified" refers to a polypeptide, protein, or other active compound that has been isolated from a cell, cell culture medium, or other crude preparation and subjected to fractionation to remove various components of the initial preparation, such as proteins, cellular debris, and other components. Such purified preparations can include materials in covalent association with the polypeptide, such as glycoside residues or materials admixed or conjugated with the polypeptide, which may be desired to yield a modified derivative or analog of the polypeptide or produce a combinatorial therapeutic formulation, conjugate, fusion protein or the like. The term purified thus includes such desired products as peptide and protein analogs or mimetics or other biologically active compounds wherein additional compounds or moieties are bound to the polypeptide in order to allow for the attachment of other compounds and/or provide for formulations useful in therapeutic treatment or diagnostic procedures.

Generally, substantially purified polypeptides, proteins, or other active compounds include more than 80% of all macromolecular species present in a preparation prior to admixture or formulation of the respective compound with additional ingredients in a complete pharmaceutical formulation for therapeutic administration. Additional ingredients can include a pharmaceutical carrier, excipient, buffer, absorption enhancing agent, stabilizer, preservative, adjuvant or other like co-ingredients. More typically, the polypeptide, protein or other active compound is purified to represent greater than 90%, often greater than 95% of all macromolecular species present in a purified preparation prior to admixture with other formulation ingredients. In other cases, the purified preparation can be essentially homogeneous, wherein other macromolecular species are less than 1%.

Receptor for advanced glycation end products (RAGE): A protein encoded by the advanced glycosylation end product-specific receptor (AGER) gene. Nucleotide and amino acid sequences of RAGE, and information on the human AGER gene can be found, for example, in the NCBI database under Gene ID 177. RAGE is a member of the immunoglobulin superfamily of cell surface receptors. It is a multi-ligand receptor, and besides AGE (advanced glycosylation end products), interacts with other molecules implicated in homeostasis, development, and inflammation, and certain diseases, such as diabetes and Alzheimer's disease. Soluble RAGE (sRAGE) refers to soluble forms of RAGE that lack the transmembrane and signaling domains. In some embodiments, sRAGE has the amino acid sequence of residues 23-360 of SEQ ID NO: 1.

Sequence identity: The similarity between amino acid or nucleotide sequences is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237-244, 1988; Higgins and Sharp, *CABIOS* 5:151-153, 1989; Corpet et al., *Nucleic Acids Research* 16:10881-10890, 1988; and Pearson and Lipman, *Proc. Natl. Acad. Sci. U.S.A.* 85:2444, 1988. Altschul et al., *Nature Genet.* 6:119-129, 1994.

The NCBI Basic Local Alignment Search Tool (BLAST™) (Altschul et al., *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx.

Variants and/or fragments of human sRAGE generally comprise at least about 80%, at least about 85%, at least about 90%, at least about 95% or at least about 99% sequence identity with a human sRAGE sequence, such the human sRAGE sequence set forth herein as SEQ ID NO: 1. When less than the entire sequence is being compared for sequence identity, fragments will typically possess at least 80% sequence identity over the length of the fragment, and can possess sequence identities of at least 85%, 90%, 95% or 99%. One of skill in the art will appreciate that these sequence identity ranges are provided for guidance only; it is entirely possible that strongly significant homologs could be obtained that fall outside of the ranges provided.

Therapeutically effective amount: A quantity of a specified agent (such as a human sRAGE polypeptide) sufficient to achieve a desired effect in a subject being treated with the agent. For example, this may be the amount of a sRAGE polypeptide useful for preventing, ameliorating, and/or treating a vascular disease, injury or inflammation. The effective amount of agent will be dependent on the subject being treated, the severity of the affliction, and the manner of administration of the therapeutic composition. For example, a therapeutically effective amount of an active ingredient (such as a sRAGE polypeptide) can be measured as the concentration (moles per liter or molar-M) of the active ingredient in blood (in vivo) or a buffer (in vitro) that produces an effect. Alternatively, the therapeutically effective amount of the agent can be measured as the weight of the agent administered (e.g. ng, mg or grams) per unit weight of the subject being administered (e.g. grams or kilograms).

Vascular disease, injury or inflammation: Any disease, disorder, condition, injury or inflammation that primarily affects the blood vessels. In some embodiments, vascular disease comprises atherosclerosis, restenosis, angina, myocardial ischemia, or any condition associated with cardiovascular inflammation. In some embodiments, vascular injuries include myocardial infarction, heart failure, traumatic injury, vascular damage caused by surgical intervention such as angioplasty or stent placement. Vascular inflammation can include inflammation of the vascular system resulting from any cause.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. An insertional vector is capable of inserting itself into a host nucleic acid. A vector can also include one or more selectable marker genes and other genetic elements. An expression vector is a vector that contains the necessary regulatory sequences to allow transcription and translation of inserted gene or genes.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

The present disclosure provides methods for producing a human sRAGE polypeptide comprising amino acid residues 23-340 of human RAGE (SEQ ID NO: 1) which has improved potency and stability as compared to the sRAGE produced by conventional methods. sRAGE is a soluble form of the RAGE protein, typically generated via alternative splicing of the AGER gene (GenBank™ Accession No. NM_172197), and by protease cleavage of cell surface RAGE to remove the membrane anchor and C-terminal cytosolic domain (see, e.g., Yonekura et al., *Biochem. J.*, 370: 1097-1109, 2003; Zhang et al., *J. Biol. Chem.*, 283: 35507-35516, 2008). Without being bound by any particular theory, sRAGE is believed to function as a decoy to compete with RAGE ligands, thereby diminishing cell signaling (see, e.g., Park et al., *Nat. Med.*, 4: 1025-1031, 1998).

Surprisingly, the expression of sRAGE in mammalian systems, such as in Chinese hamster ovary (CHO) cells, produces an sRAGE having significantly, e.g., on the order of 1000-fold, increased potency in vivo over conventionally prepared sRAGE. One conventional preparation of therapeutic sRAGE has employed a baculovirus vector in *Spodoptera frugiperda* (sf9) insect cells for expression. In some embodiments, a dose of 3 ng/g body weight for mammalian-expressed sRAGE of the present disclosure is comparable in efficacy to doses of 5000 ng/g (5 µg/g) for sRAGE expressed in sf9 insect cells. Mammalian-specific post-translational modifications, e.g., modification of the glycosylation profile, are believed to contribute to the improved stability and in vivo activity of mammalian-expressed sRAGE.

The present disclosure provides a method of producing a human sRAGE in mammalian cells. In some embodiments, the method includes (a) providing an expression vector comprising a nucleic acid sequence encoding a human sRAGE polypeptide; (b) establishing a mammalian cell with the expression vector in a medium and under conditions in which the nucleic acid sequence is expressed and the human sRAGE polypeptide is produced; and (c) isolating or purifying the human sRAGE from the medium. The sRAGE produced according to this method comprises a mammalian post-translational modification.

The mammalian cell can be any suitable mammalian cell for expression. The mammalian cell can be, for example, selected from the group consisting of CHO cells, COS cells, HEK293 cells, 3T3 cells, NS0 cells, Sp20 cells, Vero cells, HeLa cells HepG2 cells, SkHep cells, and BHK cells. In some embodiments, the mammalian cell is a CHO cell. The mammalian cell can comprise any modification deemed useful, for example in protein expression generally, or expression of the human sRAGE specifically. For example, suitable CHO cells can be dihydrofolate reductase (DHFR)-deficient, or modified to include a tetracycline repressor or an expression control vector, or have some other recombinant or selected modification. Cells suitable for use in the method of the present disclosure are capable of producing proteins having at least one post-translational modification typically understood by one of ordinary skill in the art to be associated with mammalian expression.

In some embodiments of the method, the nucleic acid sequence encoding the sRAGE polypeptide is codon-optimized for expression in a specific cell type, for example a *Cricetulus griseus* (Chinese hamster) cell, such as Chinese hamster ovary (CHO) cell. The nucleic acid molecule may also be optimized for translation. In some examples, the nucleic acid sequence encoding the sRAGE polypeptide is at least 80%, at least 85%, at least 90%, at least 95%, at least 96%, at least 97%, at least 98% or at least 99% identical to SEQ ID NO: 12. In particular non-limiting examples, the nucleic acid sequence encoding the sRAGE polypeptide comprises or consists of SEQ ID NO: 12.

In other embodiments of the method, the nucleic acid sequence encoding the sRAGE polypeptide is at least 80%, at least 85%, at least 90%, at least 95%, at least 96%, at least 97%, at least 98% or at least 99% identical to SEQ ID NO: 2 or SEQ ID NO: 9. In some examples, the nucleic acid sequence encoding the sRAGE polypeptide comprises or consists of SEQ ID NO: 2 or SEQ ID NO: 9.

The human sRAGE polypeptide prepared in accordance with the method of the present disclosure is a human sRAGE polypeptide with a mammalian post-translational modification. The human sRAGE polypeptide has an increased efficacy as compared to sRAGE proteins expressed in non-mammalian cells, especially insect cells. In some embodiments, the sRAGE can include an additional modification, such as a tag which can be used in affinity purification, e.g., a T7 tag. Optionally, such modification further includes a protease cleavage site to allow removal of such tag. The tag is then cleaved from the sRAGE sequence using an appropriate protease such as thrombin, enterokinase, or TEV protease, depending upon the chosen protease cleavage site sequence. Expression vectors suitable for use in the present disclosure include those described in U.S. Patent Application Publication 2010/0173307, which is hereby incorporated by reference.

The mammalian post-translational modification can be any post-translational modification that causes a human sRAGE produced in a mammalian cell to differ from a sRAGE produced in a non-mammalian cell, e.g., an insect cell. Such a post-translational modification can include, for example, phosphorylation, sulfation, carboxylation, hydroxylation, acetylation, myristoylation, farnesylation, ADP ribosylation, disulfide formation, and/or SUMOlyation. These modifications, when present, typically are provided in addition to a mammalian glycosylation profile. However, in some embodiments, the modifications exist even in the absence of a fully mammalian N- and/or O-linked glycosylation profile.

The mammalian post-translational modification can include a glycosylation pattern distinct from that of a non-mammalian expressed RAGE, e.g., insect expressed RAGE. RAGE is a glycoprotein having two N-glycosylation sites at residues N25 and N81, which sequons (sequences of three consecutive amino acids in a protein that can serve as the attachment site to a saccharide) have been shown to be conserved among various mammalian species (Neeper et al., *J. Biol. Chem.*, 267: 14998-15004, 1992; Pang et al., *Protein Sci.*, 18: 1261-1271, 2009). In some embodiments, the human sRAGE has mammalian glycosylation at residues N25 and/or N81. In particular examples, mammalian glycosylation is present at both residues N25 and N81 of the human sRAGE. The glycosylation profile for the mammalian-expressed sRAGE can include complex N-glycans often terminated with sialic acids (see FIG. 6), as well as galactose (see Table 2, infra). In contrast, expression of a mammalian glycoprotein in insect cells is understood to result in a post-translational modification of paucimannose N-glycans at the native sites. In addition, insect cells are unable to produce galactose and sialic acid (also termed N-acetylneuraminic acid). O-glycosylation patterns also are understood to differ between mammalian-expressed proteins and non-mammalian expressed proteins.

Accordingly, the human sRAGE may exhibit O-glycosylation patterns consistent with mammalian expression. Without being bound by any particular theory, features of the mammalian glycosylation profile (including N- and/or O-linked glycosylation) are believed to contribute to increased efficacy over sRAGE proteins expressed in other cells such as *Spodoptera frugiperda* (insect). Such features also differ from the glycosylation profile identified for N-glycans expressed in *Pichia pastoris* (yeast), which include a $Man_8GlcNAc_2$-based hypermannosyl structure (see, e.g., Vervecken et al, *Appl. Environ. Microbiol.*, 70(5): 2639-46, 2004).

The human sRAGE can be isolated or purified from the medium using any suitable isolation and/or purification methods. Suitable purification methods include affinity purification, ion exchange chromatography, high performance liquid chromatography, hydrophobic interaction chromatography, and the like.

The isolated and/or purified human sRAGE polypeptide can have any suitable purity. In some embodiments, the human sRAGE has about 80% purity or greater, e.g., about 90% purity or greater. In some examples, the human sRAGE has about 95% purity or greater, about 96% purity or great, about 97% purity or greater, about 98% purity or great, about 99% purity or greater, or about 99% purity or greater (e.g., about 100% purity). Generally, the human sRAGE is *mycoplasma*-free. The *mycoplasma* level of the human sRAGE can be measured, for example, with MYCOSCOPE™ myco-

*plasma* PCR detection kit (available from Genlatis, Inc., San Diego, Calif.) to ensure that the human sRAGE is *mycoplasma*-free.

The present disclosure also provides a method of treating a vascular disease, injury, or inflammation in a mammal. In some embodiments, the method includes administering to a mammal with a vascular disease, injury, or inflammation a human sRAGE polypeptide having a mammalian post-translational modification, or a composition comprising a human sRAGE polypeptide with a mammalian post-translational modification and a pharmaceutically acceptable carrier, thereby treating the vascular disease, injury, or inflammation in the mammal.

The post-translational modification can be any post-translational modification specific to expression in mammalian cells (see discussion above). In some embodiments, the mammalian post-translational modification comprises a modification selected from the group consisting of mammalian glycosylation, mammalian phosphorylation, mammalian sulfation, mammalian carboxylation, mammalian hydroxylation, mammalian acetylation, mammalian myristoylation, mammalian farnesylation, mammalian ADP ribosylation, mammalian disulfide formation, and mammalian SUMOylation. In some examples, the mammalian post-translational modification comprises mammalian glycosylation and/or the mammalian post-translational modification comprises a mammalian N-glycan profile.

The disclosed methods can be used to treat any disease, disorder, condition, injury or inflammation that primarily affects the blood vessels. Contemplated vascular diseases include atherosclerosis and restenosis, as well as any condition associated with cardiovascular inflammation. Contemplated vascular injuries include myocardial infarction (including acute infarction) and heart failure, as well as traumatic injury. In some embodiments, vascular injury includes vascular damage caused by surgical intervention such as angioplasty, including stent placement. Contemplated vascular inflammation can be from any cause.

sRAGE can also be used to treat Alzheimer's disease. In some embodiments, provided herein is a method of treating a mammal with Alzheimer's disease comprising administering to the mammal having Alzheimer's disease a human sRAGE polypeptide having a mammalian post-translational modification, or a composition comprising a human sRAGE polypeptide with a mammalian post-translational modification and a pharmaceutically acceptable carrier, thereby treating the Alzheimer's disease in the mammal.

The sRAGE composition to be administered to a subject having a vascular disease, injury, or inflammation can be formulated for administration by any suitable route, such as, for example, an administration route selected from the group consisting of intravenous, intraarterial, intramuscular, intraperitoneal, intrathecal, epidural, topical, percutaneous, subcutaneous, transmucosal, intranasal, and oral administration routes. In some embodiments, the composition is formulated for an intraperitoneal administration route.

A composition suitable for injectable administration can be an aqueous or nonaqueous, isotonic sterile injection solution, which can contain anti-oxidants, buffers, bacteriostats, and solutes, for example, that render the composition isotonic with the blood of the intended recipient. An aqueous or nonaqueous sterile suspension can contain one or more suspending agents, solubilizers, thickening agents, stabilizers, and preservatives. The composition can be presented in a unit-dose or multi-dose sealed container, such as ampules and vials, and can be stored in a freeze-dried (lyophilized) condition requiring only the addition of the sterile liquid carrier, for example, water, for injection, immediately prior to use. An extemporaneous injection solution or suspension can be prepared from sterile powders, granules, or tablets.

The composition can be prepared in any suitable manner. For example, a sterile injectable solution can be prepared by any suitable method, for example, by incorporating the human sRAGE polypeptide in a suitable amount in an appropriate solvent with one or a combination of the components enumerated above, as required, followed by filtered sterilization. A solution for injection preferably is essentially free of endotoxin, e.g., in an amount equal or lower than 0.5 EU/ml, which is the level that the U.S. Food and Drug Administration allows in sterile water. A dispersion of the human sRAGE generally can be prepared by incorporating the human sRAGE into a sterile vehicle which contains a basic dispersion medium and other suitable components as described above. In the case of sterile powders for the preparation of sterile injectable solutions, an exemplary method of preparation is vacuum drying or freeze-drying which yields a powder of the human sRAGE plus any additional desired components resulting from a previously sterile-filtered solution thereof.

The human sRAGE polypeptide also can be entrapped in microcapsules prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are known in the art, for example, as disclosed in Remington's Pharmaceutical Sciences, 16th edition, Osol, A., editor (Mack Publishing Co., Easton, Pa., 1980). Liposomes can be prepared by such methods as described in, for example, Rezler et al., *J. Am. Chem. Soc.*, 129(16): 4961-72, 2007; Samad et al., *Curr. Drug Deliv.*, 4(4): 297-305, 2007; and U.S. Pat. Nos. 4,485, 045 and 4,544,545. Liposomes with enhanced circulation time are disclosed in, for example, U.S. Pat. No. 5,013,556. Particularly useful liposomes can be generated by, for example, the reverse-phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Human sRAGE can be conjugated to the liposomes as described in, for example, Werle et al., *Int. J. Pharm.*, 370(1-2): 26-32, 2009.

The composition also can contain human sRAGE associated with a natural virus or virus-like particle, a dendrimer, carbon nanoassembly, a polymer carrier, a paramagnetic particle, a ferromagnetic particle, a polymersome, a filomicelle, a micelle, a lipoprotein, or various forms of nanoparticles.

The composition can be formulated for administration into the airways to provide either systemic or local administration of the human sRAGE, for example, to the trachea and/or the lungs. Such administration can be made via inhalation or via physical application, using aerosols, solutions, and devices such as a bronchoscope. For inhalation, the composition can be delivered from an insufflator, a nebulizer, a pump, a pressurized pack, or other convenient means of delivering an aerosol, non-aerosol spray of a powder, or non-aerosol spray of a liquid. Pressurized packs can comprise a suitable propellant such as liquefied gas or a compressed gas. Liquefied gases include, for example, fluorinated chlorinated hydrocarbons, hydrochlorofluorocarbons, hydrochlorocarbons, hydrocarbons, and hydrocarbon ethers. Compressed gases include, for example, nitrogen, nitrous oxide, and carbon dioxide. In particular, the use of dichlorodifluoromethane, trichlorofluoromethane, dichlorotetrafluoroethane, carbon dioxide, or other suitable gas is contemplated for such a pressurized pack. For a pressurized aerosol, the dose unit can be determined by providing a valve to deliver a controlled amount. In administering a dry powder composition, the powder mix can include a suitable powder base such as lactose or starch. The powder composition can be presented in unit dosage form such as, for example, capsules, cartridges, or blister packs from which the powder can be administered with the aid of an inhalator or insufflator.

The sRAGE composition can be formulated for transmucosal or transdermal administration. For transmucosal or transdermal administration, penetrants appropriate to the barrier to be permeated are used in or with the composition. Such penetrants are generally known in the art, and include, for example, detergents, bile salts, and fusidic acid derivatives. For transmucosal administration, the human sRAGE can be formulated into a nasal spray, inhaled aerosol, suppository, mouthwash, rapidly dissolving tablet, or lozenge. For transdermal administration, the human sRAGE can be formulated into an ointment, salve, gel, foam, or cream as generally known in the art.

The composition can be formulated for delivery using a drug delivery system, including a medicated stent, liquid suspension, ointment, complex to a bandage, collagen shield, or the like. The composition can contain hyaluronic acid or a suspension of collagen fragments. The human sRAGE can be formulated into microcapsules, designed with appropriate polymeric materials for controlled release, such as polylactic acid, ethylhydroxycellulose, polycaprolactone, polycaprolactone diol, polylysine, polyglycolic, polymaleic acid, poly[N-(2-hydroxypropyl)methylacrylamide], and the like.

The human sRAGE can be administered to the mammal in any suitable dose and in accordance with any suitable dosing regimen. In some embodiments, the human sRAGE is administered in any therapeutically effective dose and on any appropriate schedule.

A suitable dose can be determined by well-known techniques. Typically, the human sRAGE is administered at a dose of about 0.5-10 ng per gram body weight of the mammal. In some embodiments, the human sRAGE is administered at a dose of about 1-10 ng per gram body weight of the mammal. In some examples, the human sRAGE is administered at a dose of about 1.5-6 ng per gram body weight of the mammal. In particular examples, the human sRAGE is administered at a dose of about 2-4 (e.g., about 3) ng per gram body weight of the mammal. In specific non-limiting examples, the human sRAGE is administered at a dose of about 0.5, 1.0, 1.5, 2.0, 2.5, 3.0, 3.5, 4.0, 4.5, 5.0, 5.5 or 6.0 ng per gram of body weight. In other embodiments, the human sRAGE can be administered at doses greater than about 10 ng per gram of body weight of the mammal. In some examples, the sRAGE polypeptide is administered at a dose that does not exceed about 6 ng/g body weight of the mammal.

A dose of the human sRAGE can be administered to the mammal at one time or in a series of subdoses administered over a suitable period of time. In one embodiment, the human sRAGE is administered to the mammal in a single bolus dose, such as immediately following injury, e.g., before a patient is removed from surgery or while the patient is in recovery from surgery. In another embodiment, the composition can be administered in multiple doses at suitable intervals. The composition can be administered at pre-determined intervals such as prior to injury (e.g., prior to surgery), immediately following injury (e.g., immediately after surgery) and/or a suitable time following injury (e.g., post-surgery). In some cases, multiple doses of the composition are administered, such as for the treatment of a disease or disorder. For example, the composition can be administered on a daily, semi-weekly, weekly, bi-weekly, semi-monthly, bi-monthly, semi-annual, or annual basis.

In some embodiments, the human sRAGE is administered to the mammal as soon as possible after detection of the vascular disease, injury, or inflammation in the mammal, or as soon thereafter as treatment of the mammal can be arranged. For example, the human sRAGE can be administered immediately after (i.e. within about 5 minutes), or within about 30 minutes, 1 hour, 1½ hours, 2 hours, 2½ hours, 3 hours, 4 hours, 5 hours, 6 hours, 8 hours, 10 hours, 12 hours, 18 hours, or 24 hours of injury, or of the detection of vascular disease, injury, or inflammation. In some circumstances, such as where a vascular disease, injury, or inflammation been undetected or treatment was unavailable, treatment can be administered later, such as within 2, 3, 4, 5, 6, or 7 days of injury, or of detection of the vascular disease, injury, or inflammation. In situations involving vascular disease, injury, or inflammation, including ongoing morbidity after injury (including surgery), multiple doses of the human sRAGE can be administered to the patient.

For the treatment of an injury, in some embodiments, the human sRAGE is administered within about 1 hour after the injury or detection of the injury, e.g., within about 55 minutes after the injury or detection of the injury, within about 50 minutes after the injury or detection of the injury, within about 45 minutes after the injury or detection of the injury, within about 40 minutes after the injury or detection of the injury, within about 35 minutes after the injury or detection of the injury, within about 30 minutes after the injury or detection of the injury, within about 25 minutes after the injury or detection of the injury, within about 20 minutes after the injury or detection of the injury, within about 15 minutes after the injury or detection of the injury, within about 10 minutes after the injury or detection of the injury, within about 5 minutes after the injury or detection of the injury, or immediately after the injury or detection of the injury. In the event of traumatic injury, the human sRAGE can be administered as soon as medical assistance is provided to a patient, e.g., by emergency responders, emergency room personnel, etc.

The administration of the human sRAGE to a mammal can be part of a combination therapy. The phrase "combination therapy" refers to administering the human sRAGE in accordance with the present disclosure together with another therapeutic agent in a sequential or concurrent manner such that the beneficial effects of the combination are realized in the mammal undergoing treatment.

Any suitable mammal can be treated in accordance with the treatment method of the present disclosure. In some embodiments, the mammal is a human. In other embodiments, the mammal is a non-human primate, or another mammal such as a pig, horse, cow, dog, cat, rabbit, rat, or mouse. Any suitable animal model can be used in testing the treatment method of the present disclosure.

In some embodiments, the amino acid sequence of the sRAGE polypeptide to be administered is at least 80%, at least 85%, at least 90%, at least 95%, at least 96%, at least 97%, at least 98% or at least 99% identical to amino acid residues 23-340 of SEQ ID NO: 1. In some examples, the amino acid sequence of the sRAGE polypeptide comprises or consists of amino acid residues 23-340 of SEQ ID NO: 1. In other embodiments, the amino acid sequence of the sRAGE polypeptide is at least 80%, at least 85%, at least 90%, at least 95%, at least 96%, at least 97%, at least 98% or at least 99% identical to SEQ ID NO: 4, SEQ ID NO: 10 or SEQ ID NO:

11. In some examples, the amino acid sequence of the sRAGE polypeptide comprises or consists of SEQ ID NO: 4, SEQ ID NO: 10 or SEQ ID NO: 11.

The present disclosure also provides isolated or purified human sRAGE polypeptides having a mammalian post-translational modification, as well as compositions comprising the mammalian-expressed human sRAGE (i.e., an isolated or purified human sRAGE with a mammalian post-translational modification) and a pharmaceutically acceptable carrier. The composition can contain additional components, such as, for example, diluents, adjuvants, excipients, preservatives, pH adjusting agents, and the like, as well as additional therapeutic agents, such as, for example, therapeutic agents useful in the treatment of a particular indication (e.g., other therapeutic agents for controlling inflammation such as steroids or NSAIDs). Desirably, the additional components do not significantly negate the effect of the human sRAGE as administered to a mammal to treat a vascular disease, injury, or inflammation in accordance with the present disclosure. Compositions comprising a human sRAGE polypeptide are described in detail above.

In some embodiments, the isolated human sRAGE polypeptide comprises an amino acid sequence that is at least 80%, at least 85%, at least 90%, at least 95%, at least 96%, at least 97%, at least 98% or at least 99% identical to amino acid residues 23-340 of SEQ ID NO: 1. In some examples, the amino acid sequence of the isolated sRAGE polypeptide comprises or consists of amino acid residues 23-340 of SEQ ID NO: 1. In other embodiments, the amino acid sequence of the sRAGE polypeptide is at least 80%, at least 85%, at least 90%, at least 95%, at least 96%, at least 97%, at least 98% or at least 99% identical to SEQ ID NO: 4, SEQ ID NO: 10 or SEQ ID NO: 11. In some examples, the amino acid sequence of the sRAGE polypeptide comprises or consists of SEQ ID NO: 4, SEQ ID NO: 10 or SEQ ID NO: 11.

Further provided by the present disclosure are nucleic acid molecules encoding a human sRAGE polypeptide that is codon-optimized for expression in *Cricetulus griseus* (Chinese hamster) cells, such as CHO cells. In some embodiments, the isolated nucleic acid molecule comprises at least 80%, at least 85%, at least 90%, at least 95%, at least 96%, at least 97%, at least 98% or at least 99% sequence identity to the nucleotide sequence of SEQ ID NO: 12. In particular examples, the isolated nucleic acid molecule comprises or consists of the nucleotide sequence of SEQ ID NO: 12. Also provided are vectors comprising the disclosed nucleic acid molecules. Isolated mammalian host cells comprising the disclosed vectors are also provided by the present disclosure. In some examples, the mammalian cell is a CHO, COS, HEK293, 3T3, NS0, Sp20, Vero, HeLa, HepG2, SkHep or BHK cell. In particular non-limiting examples, the cell is a CHO cell.

The following examples are provided to illustrate certain particular features and/or embodiments. These examples should not be construed to limit the disclosure to the particular features or embodiments described.

EXAMPLE 1

This example demonstrates the expression of recombinant sRAGE in a mammalian cell and purification therefrom.

A mammalian sRAGE expression module (SEQ ID NO: 2) encoding a polypeptide having the following features, from N-terminus to C-terminus, (1) RAGE signal peptide (residues 1-22 of SEQ ID NO: 1); (2) linker comprising Glu-Phe; (3) T7 epitope tag (SEQ ID NO: 3); (4) linker comprising Gly-Ser; and (5) ectodomain of RAGE (residues 23-340 of SEQ ID NO: 1), was subcloned into the pcDNA 3.1 expression vector by standard molecular biology techniques. When expressed in mammalian cells, the RAGE signal peptide and the Glu-Phe linker are cleaved in the endoplasmic reticulum, resulting in a T7-Gly-Ser-RAGE (23-340) polypeptide (SEQ ID NO: 4) which is secreted from the host cells (see Pang et al., *Protein Sci* 18: 1261-1271, 2009).

Chinese hamster ovary cells (CHO-CD14) were transiently transfected with the sRAGE expression vector or a vector encoding full-length (FL) RAGE tagged with the T7 epitope using Lipofectamine® or Lipofectamine® 2000 transfection reagent (Invitrogen, Carlsbad, Calif.) according to manufacturer's instruction. After overnight culture, the cell lysates and culture media were harvested and the protein concentration in each sample was determined by standard colorimetric assays. Samples of the cell lysates and culture media (5 µg protein) were subjected to sodium dodecyl sulfate polyacrylamide gel electrophoresis (SDS-PAGE), and immunoblotted with anti-T7 antibodies. Transient expression of sRAGE in CHO-CD14 cells resulted in the accumulation of sRAGE protein in the cell lysates, as well as the secretion of sRAGE into the culture medium. In contrast, transient expression of RAGE (FL) resulted in the accumulation of RAGE (FL) in the cell lysates, but not in the culture medium (FIG. 1A).

CHO-CD14 cells stably expressing sRAGE were generated by transfection with the sRAGE expression vector, followed by selection with 500 µg/mL zeocin (Invitrogen, Carlsbad, Calif.) for 10-14 days. Individual zeocin-resistant colonies were isolated and grown in separate plates. The culture media from each plate was collected, and the secretion of sRAGE was monitored by immunoblotting as described above. Stable cell lines with a high yield of sRAGE were used for production and purification of recombinant sRAGE.

To prepare and purify recombinant human sRAGE, culture medium was collected daily from stably transfected cells, and sRAGE was purified using the Novagen T7 tag affinity purification kit (EMD Biosciences, San Diego, Calif.) according to the manufacturer's instructions. The input, flow through, and elution fractions (15 µL each) were resolved by SDS-PAGE, and immunoblotted with anti-T7 antibodies to monitor the purification steps (FIG. 1B). sRAGE present in elution fractions 2 and 5 was highly purified, as evidenced by the absence of additional protein bands on silver-stained SDS-PAGE gels (FIG. 1C). The endotoxin levels of the purified sRAGE preparations were determined using the TOXINSENSOR™ Chromogenic LAL Endotoxin Assay Kit (Genscript, Piscataway, N.J.) according to the manufacturer's instructions. The sRAGE preparations utilized in the experiments described herein were determined to contain endotoxin levels lower than 0.5 EU/mL.

The *mycoplasma* levels of the purified sRAGE preparations were determined using the MYCOSCOPE™ *Mycoplasma* PCR Detection Kit (Genlantis, San Diego, Calif.) according to the manufacturer's instructions. The sRAGE preparations utilized in the experiments described herein were determined to contain undetectable amounts of the 21 *mycoplasma* species which are capable of being detected by the MYCOSCOPE™ kit. Purified recombinant sRAGE was stored in aliquots at −80° C. until use.

These results demonstrate that mammalian cells transfected with a construct encoding human sRAGE can express the construct to provide human sRAGE, that the human sRAGE is secreted into the culture medium, and that the human secreted sRAGE can be purified from the culture medium.

EXAMPLE 2

This example demonstrates various pharmacokinetic properties of injected recombinant sRAGE produced in mammalian cells.

To measure in vivo pharmacokinetic effects of injected sRAGE, male Wistar rats (350-400 g) were anesthetized with 2% isoflurane, and then injected with 7 ng/g purified sRAGE either intraperitoneally or intravenously. At various time points, blood was drawn from the femoral vein using a catheter, and centrifuged to obtain the serum. sRAGE in the serum was assayed with a Quantikine ELISA kit (R&D Systems, Minneapolis, Minn.), which is specific to human sRAGE and displays less than 2% cross reactivity to rat sRAGE.

Peak serum levels of sRAGE were observed shortly after injection, and declined rapidly thereafter regardless of the route of injection. In particular, peak serum levels of sRAGE administered intraperitoneally occurred at about 17 minutes post injection, whereas peak levels of sRAGE administered intravenously appeared at about 5 minutes post injection (FIG. 2).

The results of this example demonstrate the pharmacokinetic properties of recombinant sRAGE produced in accordance with the methods of the present disclosure.

EXAMPLE 3

This example describes the generation of an unglycosylated sRAGE mutant and its biochemical characterization in vitro.

RAGE is a glycoprotein with two potential N-glycosylation sites: residues N25 and N81, both of which are well-conserved among different mammalian species (Neeper et al., *J. Biol. Chem.* 267: 14998-15004, 1992; Pang et al., *Protein Sci* 18: 1261-1271, 2009). To test whether N-glycosylation plays a role in the observed high potency of recombinant sRAGE produced in mammalian cells, sRAGE constructs carrying a single N25T or N81T mutation, or a double N25T/N81T mutation were generated by PCR-based mutagenesis using the primers listed in Table 1.

TABLE 1

| Primer | Sequence | SEQ ID NO: |
|---|---|---|
| N25T-forward | GAAGATCTGCTCAAACCATCACAGC CCGGATTGGC | 5 |
| N25T-reverse | Phos-GGGAAGGACACGAGCCAC | 6 |
| N81T-forward | Phos-ACCGGCTCCCTCTTCCTTCCG | 7 |
| N81T-reverse | GCTCTAGATCAAGTTCCCAGCCCTG | 8 |

One primer from each set was phosphorylated (Phos) at the 5'-end to facilitate blunt end ligation into a pJP008 (Pang et al., *Protein Sci.* 18: 1261-1271, 2009) vector via ligation of the BamHI/BglII-XbaI sites.

The N25T, N81T, and N25T/N81T constructs were subcloned into an expression vector, which tagged each expressed protein with a T7 tag, and transiently transfected into CHO-CD14 cells. The cell culture media was harvested, treated with PNGase F, resolved on SDS-PAGE, and immunoblotted with anti-T7 antibodies, as described previously (Pang et al., *Protein Sci.* 18: 1261-1271, 2009). Cell culture medium from CHO-CD14 cells transfected with the N25T or N81T single mutant contained glycosylated sRAGE, which was effectively deglycosylated by PNGase F treatment (FIG. 3). In contrast, cell culture medium from CHO-CD14 cells transfected with the N25T/N81T double mutant contained unglycosylated sRAGE exclusively.

For further characterization of the N25T/N81T mutant, recombinant protein was produced by transiently expressing the N25T/N81T protein in CHO-CD14 cells, and purifying the N25T/N81T protein from the culture medium using the Novagen T7 tag affinity purification kit (EMD Biosciences, San Diego, Calif.), as described in Example 1.

To determine the ligand binding capacity of the N25T/N81T mutant, an HMGB1 ELISA assay was performed as described previously (Liu et al., *Acta Med. Okayama* 63: 203-211, 2009). sRAGE (N25T/N81T) exhibited a dissociation constant (Kd) over 10 times that of the wild-type sRAGE (520.6 nM versus 49.45 nM), suggesting that N-glycosylation of sRAGE is important for its ligand-binding capacity in vitro.

Figure 4A:
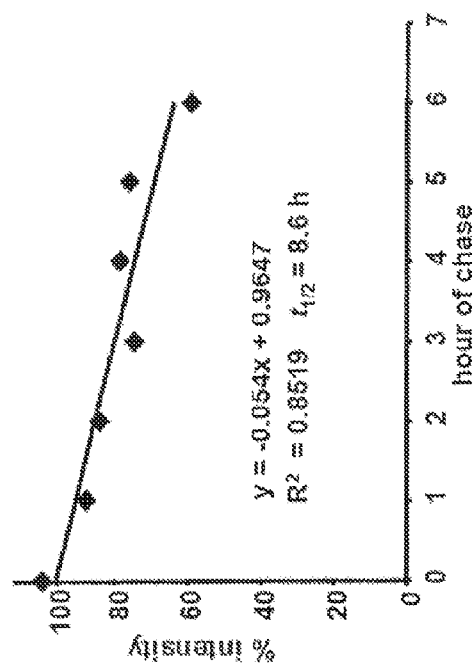
FIGS. 4A-4B are immunoblots (left) depicting RAGE expression in CHO cells transiently transfected with RAGE (WT) (FIG. 4A) or RAGE (N25T/N81T) (FIG. 4B) at various time points following 200 μg/mL cycloheximide treatment. Also shown are the corresponding graphs (right) depicting the protein half-life calculation.
Figure 4B:
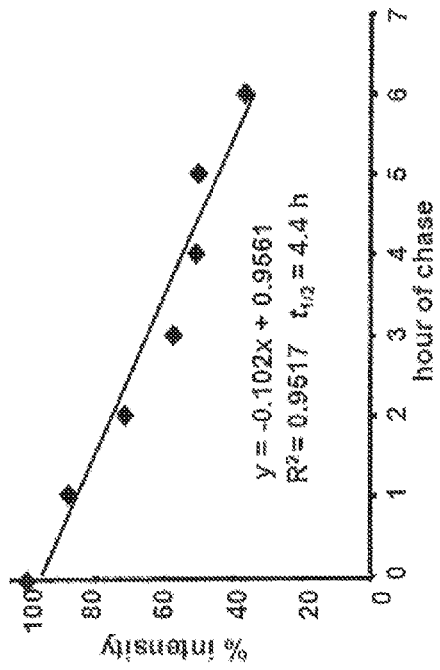
Figure 7A:
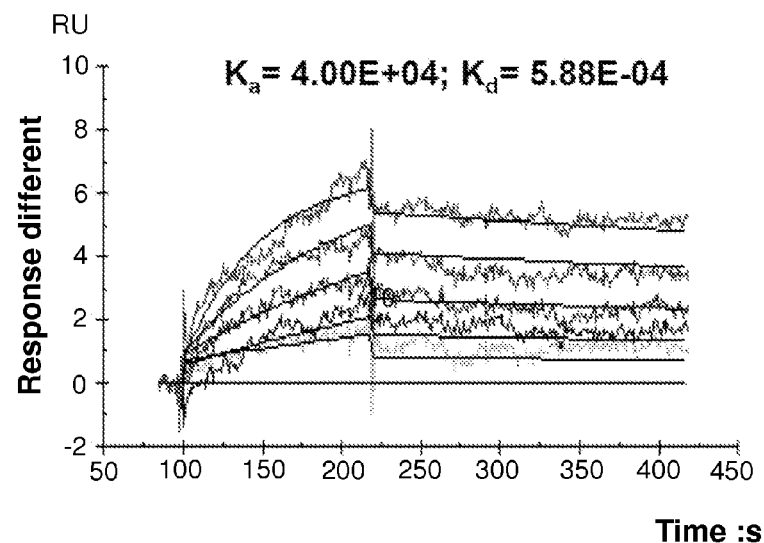
FIGS. 7A-7H are graphs (sensorgrams) showing BIAcore™ surface plasmon resonance studies of sRAGE-ligand interactions.
Figure 7B:
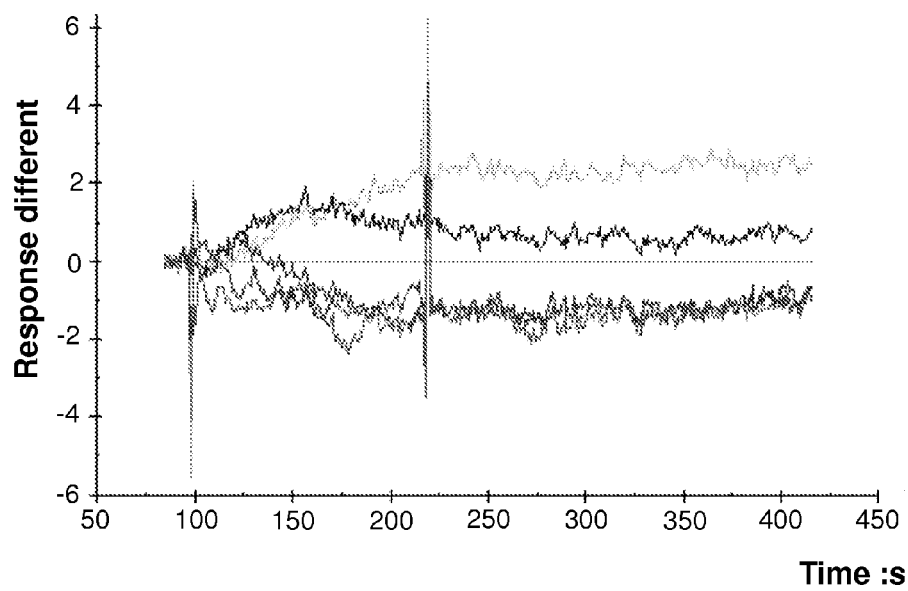
Figure 7C:
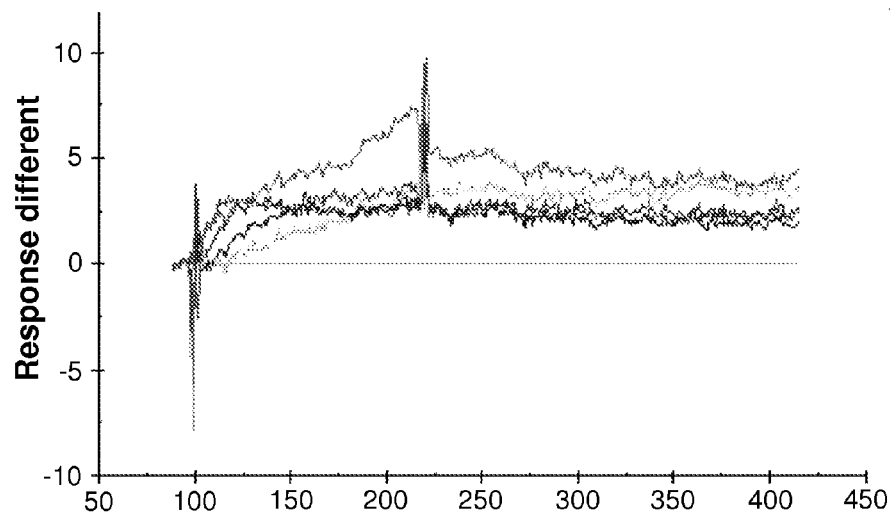
Figure 7D:
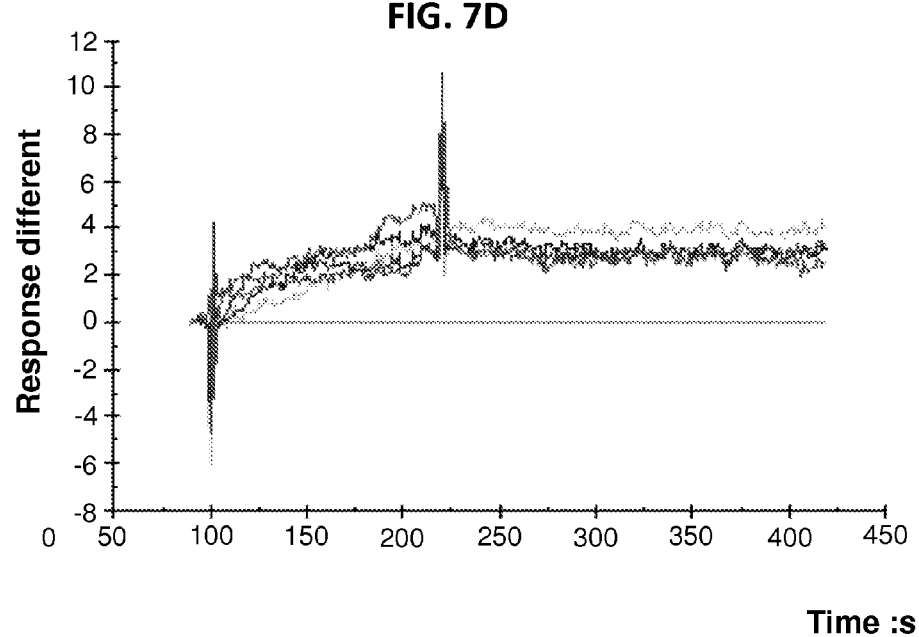
Figure 7E:
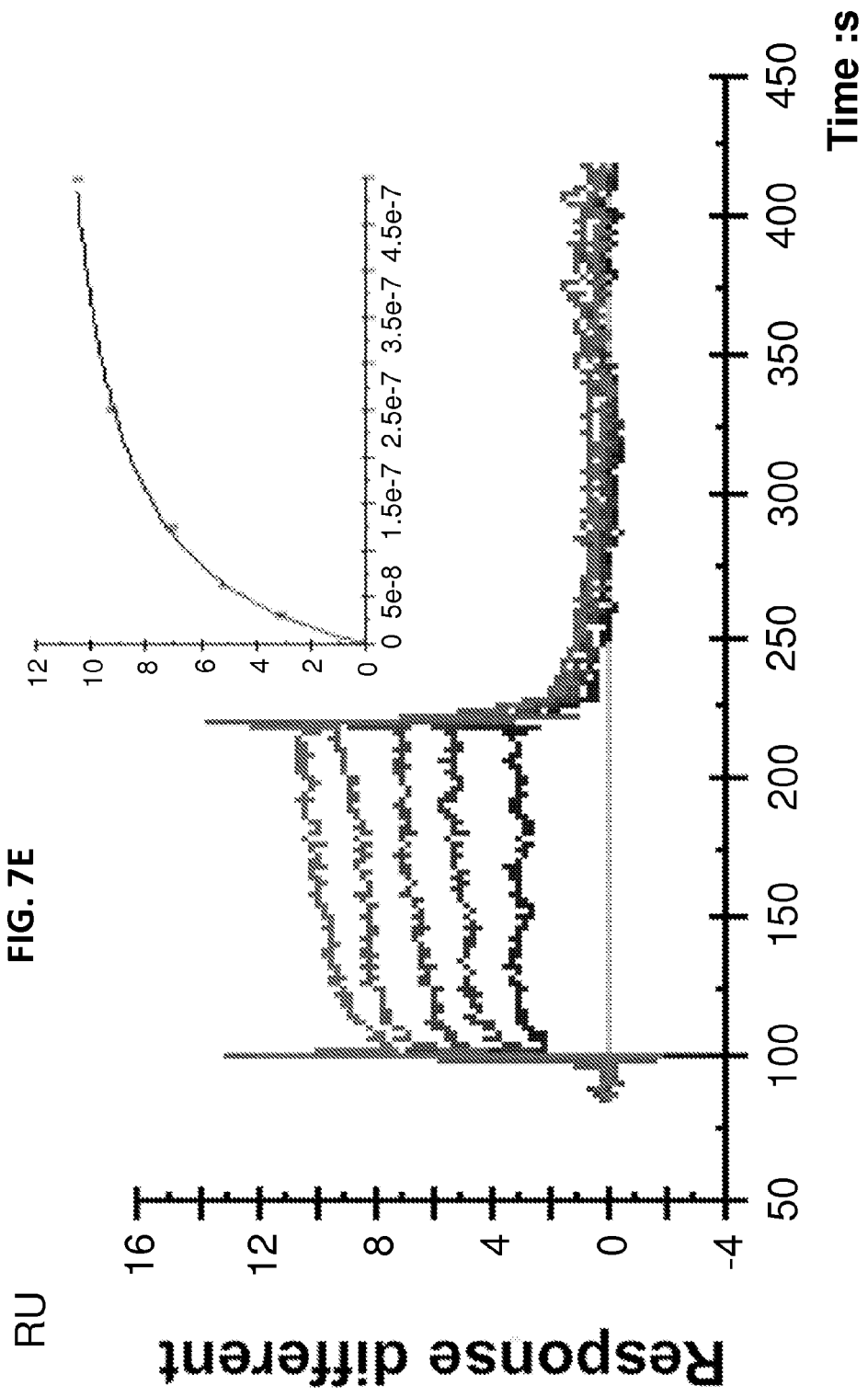
Figure 7F:
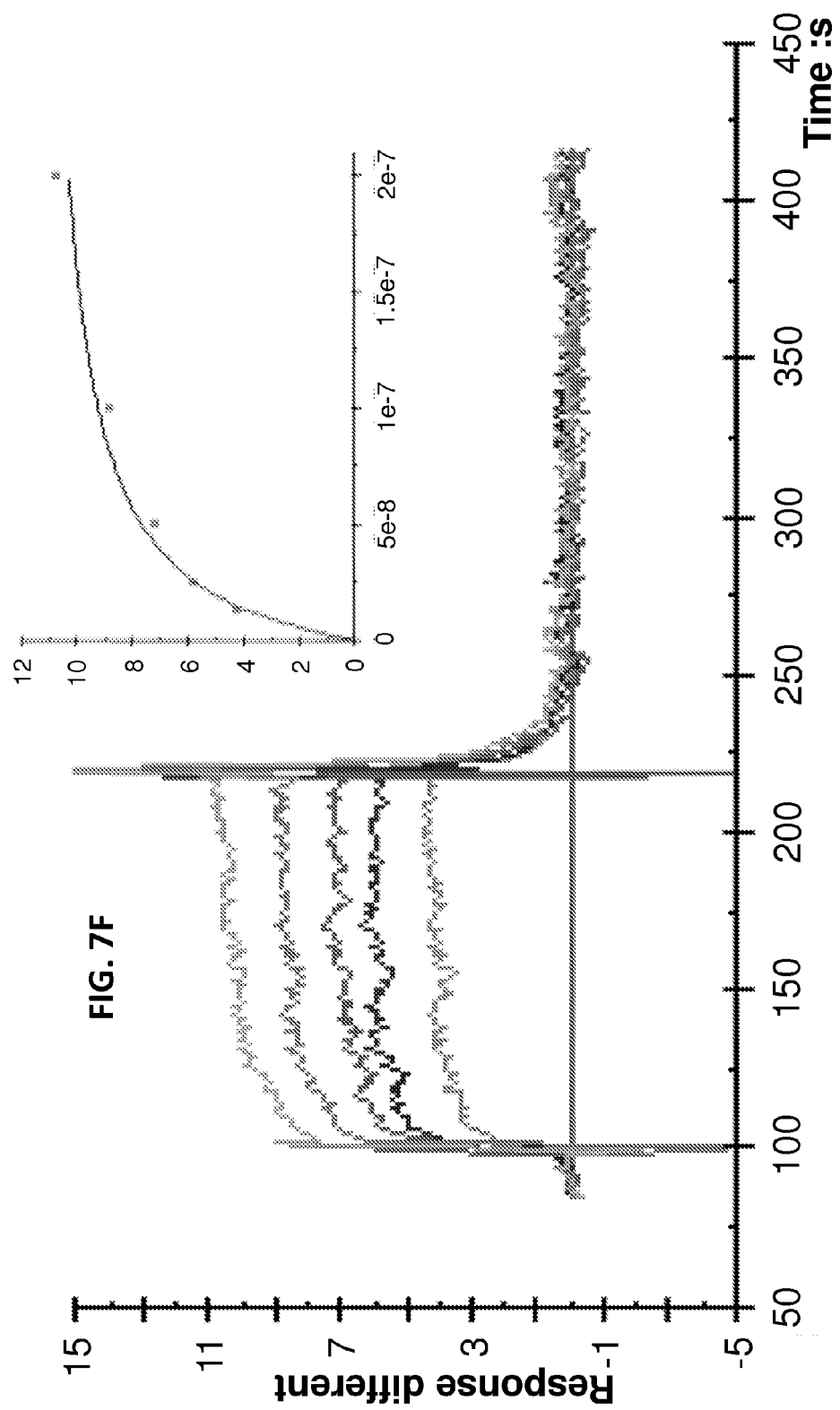
Figure 7G:
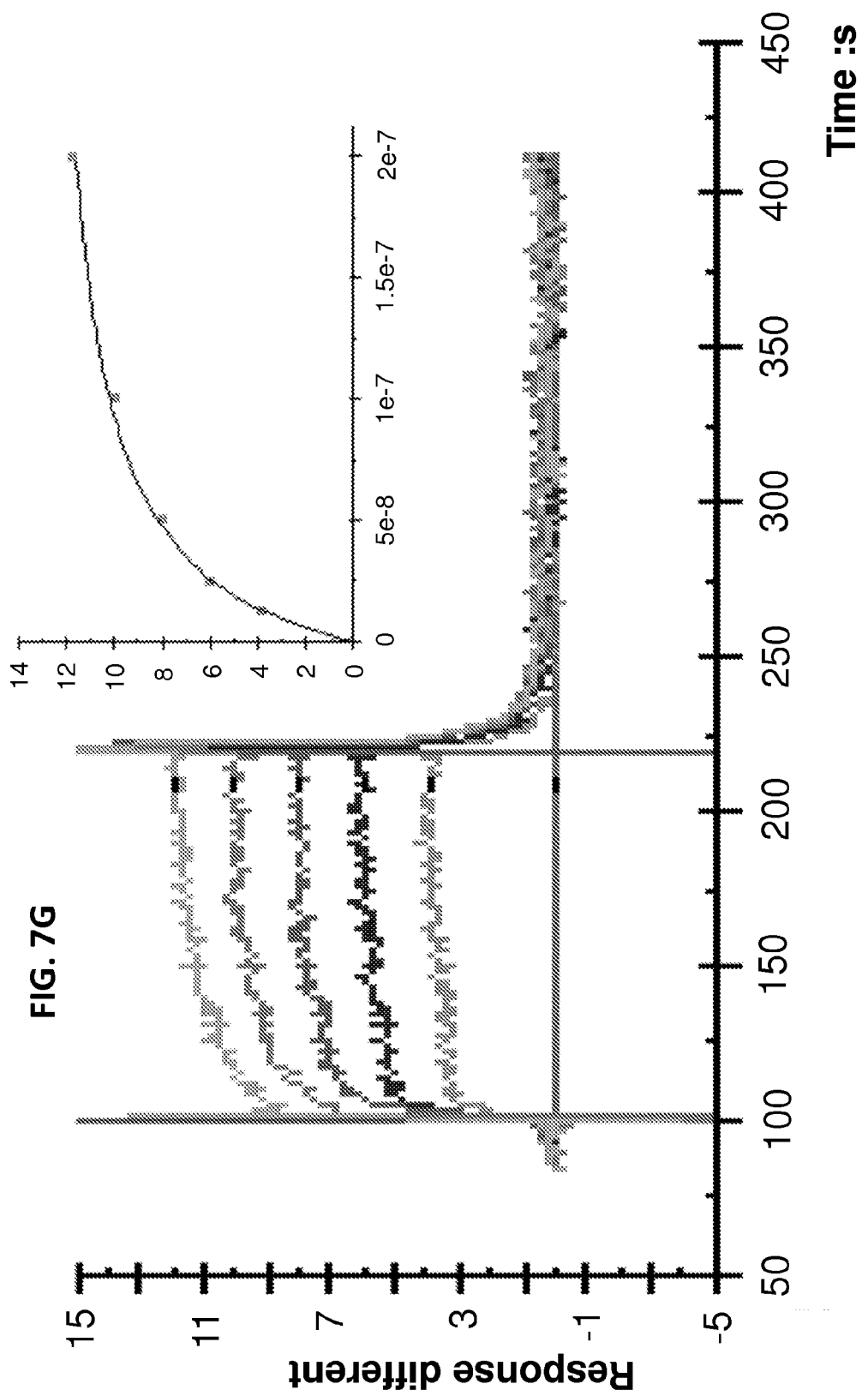
Figure 7H:
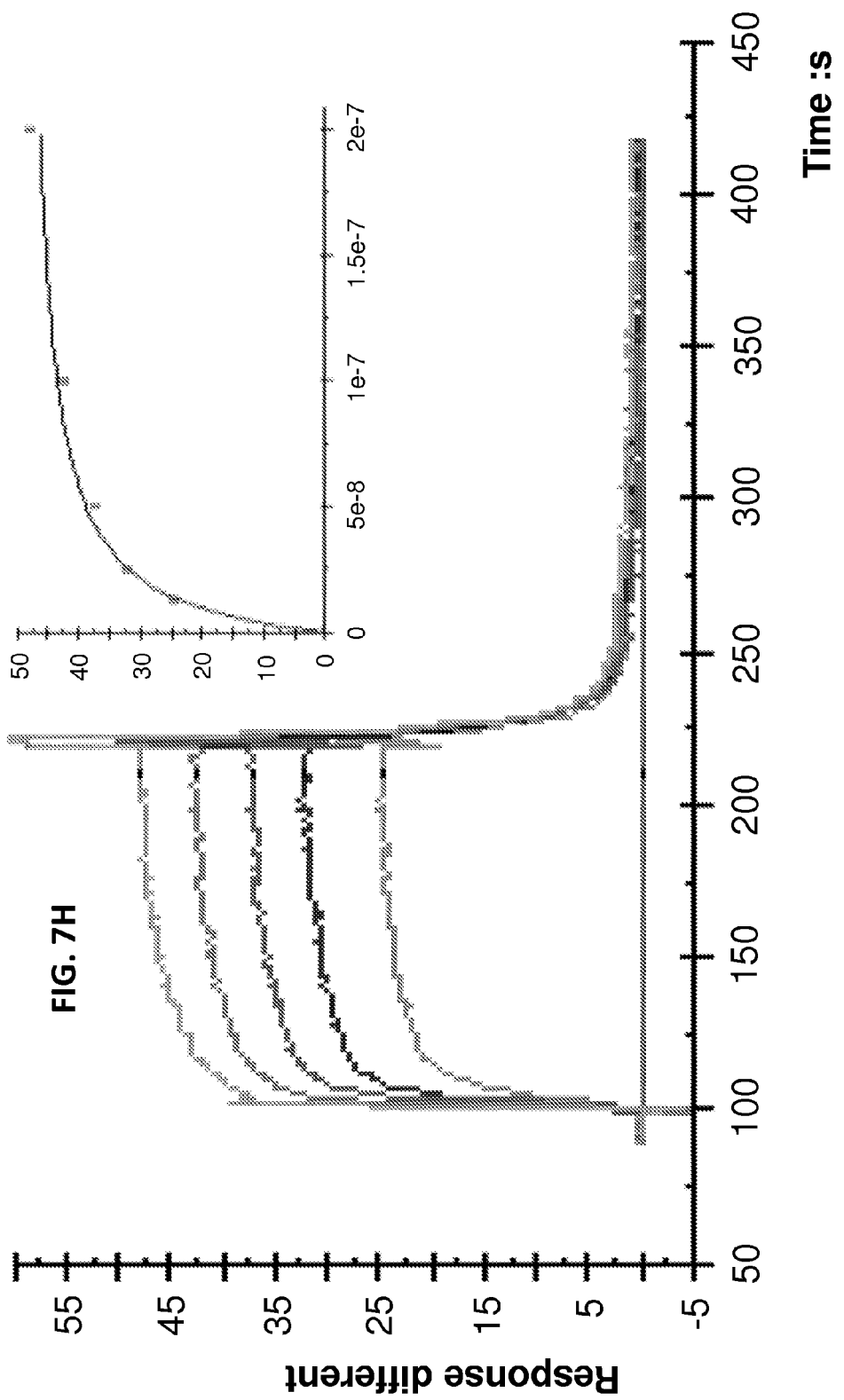

The in vitro stability of the N25T/N81T mutant was analyzed using a cycloheximide chase assay. Briefly, CHO-CD14 cells were seeded in individual 35 mm cell culture plates and transfected with an expression vector encoding RAGE (WT) or RAGE (N25T/N81T). On the next day, the cells were washed once with 1×PBS and replenished with fresh RPMI 1640 medium containing cycloheximide (200 µg/ml). At each time point, cells were lysed and processed for SDS-PAGE and immunoblotting with anti-RAGE antibodies. The intensity of the RAGE band at each time point was measured and computed as the percentage relative to the 0 time point (as 100%). Wild-type RAGE had a longer half-life ($t_{1/2}$=8.6 hr) (FIG. 4A) than RAGE (N25T/N81T) ($t_{1/2}$=4.4 hr) (FIG. 4B), suggesting that N-glycosylation contributes to the stability of sRAGE in vitro.

These results confirm that N-glycosylation of sRAGE contributes to its ligand binding and stability properties in vitro.

EXAMPLE 4

This example demonstrates the preparation of a mammalian-expressed sRAGE containing a cleavable tag sequence.

A T7-sRAGE expression vector was engineered to contain a thrombin cleavage site engineered between an $NH_3$-terminal T7 epitope tag and the sRAGE amino acid sequence (SEQ ID NO: 9). The expression vector was transfected into CHO-CD14 cells and the sRAGE product (SEQ ID NO: 10) was purified using T7 affinity chromatography as described in Example 1. The T7 tag was then cleaved from the sRAGE sequence by thrombin treatment to produce an untagged sRAGE product (SEQ ID NO: 11).

The results of this example demonstrate a method to prepare an untagged sRAGE in mammalian cells.

EXAMPLE 5

This example describes the finding that the N-glycan structure of sRAGE is a key determinant of its therapeutic potency to attenuate injury-elicited arterial inflammation and neointimal growth.

Materials and Methods

Carbohydrate Profiling of sRAGE$^{CHO}$ with High-Performance Anion-Exchange Chromatography (HPAEC)

Purified sRAGE$^{CHO}$ was hydrolyzed and analyzed with by HPAEC using a Carbopac PA1 column with pulsed amperometric detection as described previously (Fan et al., *Anal Biochem* 219:375-378, 1994). Briefly, PNGase F was used to release N-glycans from sRAGE$^{CHO}$. The released N-glycans were purified with a SEPHAROSE™ CL-4B column, and resolved by HPAEC on a CARBOPAC™ PA-100 column (Dionex). The elution positions of N-glycans were compared to N-glycan standards (bovine ribonuclease B for high-mannose type glycans, human IgG for neutral complex-type glycans, and human transferrin for sialylated complex-type glycans) (Tomiya et al., *Anal Biochem* 163:489-499, 1987). For chemical desialylation, N-glycans were treated with 20 mM HCl at 55° C. for 30 minutes prior to HPAEC analysis.

NF-κB-Luciferase Reporter Assays

Dual-luciferase reporter assay system (Promega) was used to monitor NF-κB activity, according to the manufacturer's instructions. Briefly, expression vectors harboring the firefly luciferase gene controlled by NF-κB cis-element (pNF-κB-luciferase) and *Renilla* luciferase (pRL-SV40) were transfected to HEK293 or HEK293-RAGE cells in 24-well cell culture plates at a ratio of 1:7. The transfected cells were incubated in 1% serum supplemented medium for 24 hours, and were treated with RAGE ligands (100 nM) and sRAGEs (100 nM) for 2 hours in serum-free medium followed by luciferase activity assays. NF-κB activity (triplicate) measured was normalized with *Renilla* luciferase activity, and calculated as inhibition percentage.

Affinity Purification of sRAGE

Cell culture medium was collected daily from transient or stably-transfected CHO cells, or sRAGE-baculovirus infected sf9 cells, and centrifuged at low speed to remove dead cells. Novagen T7 tag affinity purification kit was used to purify sRAGE, according to the manufacturer's instructions. The 5 fractions (1 ml of each) were collected, and fractions 2-4 were pooled. To monitor the purification steps, the input medium and individual fraction (15 µl of each) were resolved with 4-12% gradient SDS-PAGE and probed with anti-T7 antibodies. A silver stain kit (Thermo Scientific) was used to stain the resolved samples to monitor the purity of the fractions. The concentration of purified sRAGE was assayed using a RAGE ELISA kit from R & D Systems, and the protein was stored in aliquots at −80° C. The purity of sRAGE, after affinity purification, was estimated to be about 80-85%. For sRAGE$^{CHO}$(desialylation), cell medium containing sRAGE$^{CHO}$ was bound to anti-T7 agarose beads, washed, and equilibrated with G1 neuraminidase buffer (New England Biolabs), and cleaved with 50-100 units neuraminidase at 37° C. for 1 hour with constant shake. The beads were then washed and eluted as described. Desialylation was monitored with SDS-PAGE followed with western blotting using untreated T7-sRAGE as a control. Prior to injection into animals, the sRAGE preparations were tested for endotoxin level using ToxinSensor™ Chromogenic LAL Endotoxin Assay Kit from Genscript to assure that the endotoxin level was below 0.5 EU/ml, and free of *mycoplasma* (tested with Mycoscope™ *mycoplasma* PCR detection kit from Genlatis).

Carotid Artery Balloon Denudation Injury Model

Male Wistar rats (400-450 g) were administered 3% isoflurane for anesthesia, and a neck midline incision was made to expose the left carotid artery. Fogarty balloon catheter (Edwards Lifesciences) was inserted into the external carotid branch to the aortic arch and insufflated to produce slight resistance. The catheter was then withdrawn 3 times to produce sufficient injury on the endothelium.

Histomorphological Analyses

Rats were euthanized 2 weeks post-surgery. Immediately following sacrifice, the thorax cavity was opened. Through an incision on the right ventricle, the vasculature was flushed with saline until clear, and replenished with 10% NBF. The organs and aorta were then harvested. The aorta was dissected free from the surrounding connective tissue and further fixed in 10% NBF. Cross-sections of the aorta, 2-3 mm in length, were taken from aortic-arch to bifurcation region (internal and external carotid artery), processed, and embedded in paraffin to be further cut to 7 µm thin sections for H&E staining and immunohistochemistry. Morphological analyses of carotid artery segments were performed with a digital imaging analysis system (MCID, GE Healthcare). Doses and preparations of sRAGE and placebo in the studies were blinded to the investigators performing the injections and histomorphological analyses to obtained unbiased assessments.

Immunohistochemistry

Standard avidin-biotin complex (ABC) method was used. Briefly, vessel sections were deparaffinized with xylene and rehydrated through gradient ethanol immersion. Antigen retrieval was performed by microwaving the sections for 5 minutes in citric acid buffer (2 mM citric acid and 9 mM trisodium citrate dehydrate, pH 6.0). After washing with PBS, the slides were treated with peroxidase blocking buffer for 5 minutes to quench endogenous peroxidase activity and blocked with 2% bovine serum albumin (BSA) at room temperature for 1 hour followed with washing and incubation with primary antibodies. Rabbit polyclonal anti-RAGE, anti-s100, and anti-HMGB1 (all with 1:1,000 dilution), and mouse monoclonal anti-ICAM-1 antibodies (1:100) were from Abcam (Cambridge, Mass.), rat monoclonal anti-VCAM-1 antibodies (1:100) were a product from Covance (Princeton, N.J.). The specimen were then incubated with biotinylated secondary antibodies, washed with PBS containing 0.02% Tween-20, and reincubated with streptavidin-horseradish peroxidase for detection. The sections were counterstained with hematoxylin, rinsed, dehydrated and mounted with mounting medium. The staining was visualized with diaminobenzidine liquid substrate system (Dako).

Statistical Analyses

Data were analyzed using one-way variance (ANOVA) followed with Duncan's post hoc comparison from software SAS 9.1. $p<0.05$ was considered significant.

Subcloning of sRAGE and Establishing Stably Transfected Cell Lines

Human RAGE cDNA sequence encoding for residues 23-340 was amplified by PCR, and the fragment was subcloned into an expression vector that epitope-tags, and targets cloned protein to the cell surface (Pang et al., *Protein Sci* 18:1261-1271, 2009). This portion of RAGE encompasses the entire ectodomain of RAGE. Both transient and stable transfections of the construct were conducted with Lipofectamine or Lipofectamine 2000 (Invitrogen) according to manufacturer's instructions. For establishing stably transfected sRAGE cell lines in CHO-CD14 cells, the transfected cells were treated with trypsin after overnight incubation in 5% $CO_2$, 37° C. incubator, and reseeded with different dilutions in 100 mm tissue culture plates. Zeocin (500 µg/ml, Invitrogen) was added into RPMI1640 medium as the selection reagent. The cells were maintained with zeocin for 10-14 days with periodic medium changes. Individual zeocin-resistant colonies were isolated and grown in separated plates. The cell culture media were then collected from each plate, and the secretion of sRAGE was monitored with western blotting, using anti-T7 antibodies. Cell lines with high yield of sRAGE were stocked and maintained for scaled-up productions. An HEK293 cell line that stably expresses FLAG-RAGE was established with Invitrogen Flp-in system, according to the manufacturer's instructions.

Expression of sRAGE in Sf9 Cells

Baculovirus carrying human T7-sRAGE cDNA was constructed with Baculovirus Expression System with Gateway® Technology kit (Invitrogen), using pENTR1 vector.

The constructed virus was used to infect sf9 cells and the medium was collected and affinity-purified as described.

Determination of Concentration, Endotoxin and *Mycoplasma* Level of Purified sRAGE The concentration of purified sRAGE was determined by a protein colorimetric assay kit (Thermo Scientific), according to the manufacturer's instructions. To insure that the actual sRAGE dose used for injection was not underestimated, purified sRAGE was also resolved with 4-12% gradient SDS-PAGE, and compared with co-resolved BSA standard by staining with Coomassie Blue R-250. The endotoxin level of the purified sRAGE was determined with ToxinSensor™ Chromogenic LAL Endotoxin Assay Kit from Genscript. All sRAGE preparations contained endotoxin lower than 0.5 EU/ml. The *mycoplasma* level was measured with Mycoscope™ *mycoplasma* PCR detection kit from Genlatis to assure that the sRAGE preparation was *mycoplasma*-free. This kit detects 21 *mycoplasma* species.

Vessel Ultrasound Sonography

Vessel ultrasound sonography was conducted on the 7$^{th}$ and 14$^{th}$ days post-surgery. Rats were sedated with isoflurane (2% in oxygen) via face masks, and put in a supine position. After shaving frontal neck skin hair, a 40 MHz probe was used to scan the carotid arteries. M-mode tracing was recorded at 3 points: 3 mm and 10 mm distal to the base, and 2 mm proximal to the bifurcation, in long-axis view. Each M-mode tracing includes the whole vessel wall and lumen. Vessel wall was also recorded alone using a zoom-in function. B-mode was recorded at 2 mm proximal to the bifurcation. The vessel wall thickness and lumen diameter at minimal and maximal points were measured using an NIH imaging software off-line. The parameters from the non-operated right carotid artery of the same subjects were used as normal controls.

Western and Deglycosylation Assays

Western and PNGase F deglycosylation assays were performed as previously described (Pang et al., *Protein Sci* 18:1261-1271, 2009).

In Vivo Pharmacokinetics of Injected sRAGE

Male Wistar rats (350-400 g) were anesthetized with 2% isoflurane, and 7 ng/g purified sRAGE was injected either intraperitoneally or intravenously. At various time points, blood was drawn from the femoral vein using a catheter, and centrifuged to obtain serum. sRAGE in the serum was assayed with a Quantikine ELISA kit (R & D System) specific for human sRAGE (less than 2% cross reactivity to rat sRAGE).

Generation of sRAGE(N25T/N81T)

sRAGE (N25T/N81T) was generated using two sets of primers via PCR (SEQ ID NOs: 5-8), each with one of the primers phosphorylated at 5' to facilitate the blunt end ligation (see Example 3).

```
Set 1 - N25T portion:
Forward:
5' GAAGATCT GCT CAA ACC ATC ACA GCC CGG ATT GGC 3'
   BglII    23  ↕
                A
Reverse: 5'-Phos-GGG AAG GAC ACG AGC CAC 3'
                  80
```

```
Set 2 - N81T portion:
Forward: 5'-Phos-ACC GGC TCC CTC TTC CTT CCG 5'
                 ↕
                 A
                 81

Reverse: 5'GCTCTAGA TCA AGT TCC CAG CCC TG 5'
            XbaI   Stop 340
```

The numbers beneath the sequences mark the corresponding amino acid number in sRAGE protein. The mutated nucleotide and the introduced restriction sequences are underlined. The wild-type sRAGE construct was used as the template for both PCR sets. The two amplified fragments were purified with QIAquick PCR purification kit (Qiagen), and ligated with T4 DNA Quick ligase (New England Biolabs). The Quick-ligated mixture was then used as the template for re-amplification by PCR, using the forward primer from Set 1 and the reverse primer from Set 2. The re-amplified full-length sRAGE sequence carrying the two mutations was inserted to pJP008 (Pang et al., *Protein Sci* 18:1261-1271, 2009) vector via ligation of BamHI/BglII-XbaI sites. The construct was nucleotide-sequenced to confirm the mutations. The single site mutation was generated by a similar process with one of the forward primers carrying the wild-type sequence.

Surface Plasmon Resonance (SPR) Studies

Purified sRAGEs (1 μg) were diluted in degassed HBS-P buffer (10 mM HEPES, pH 7.4, 150 mM NaCl, and 0.05% surfactant P20) and immobilized to the surface of a BIAcore™ CM5 sensor chip (BIAcore Inc., New Jersey) via amine-coupling, according to the manufacturer's instructions (GE Healthcare). After surface blocking reaction with 1 M ethanolamine and washing, RAGE ligands HMGB1 (Sigma) diluted in HBS-P buffer to the indicated concentrations were injected to the channels of the chip with a flow rate of 30 μl/min at 25° C., and the sensorgrams were recorded with BIAcore™ 3000. The flow cell in the same chip activated with 0.1 M N-hydroxysuccinimide and 0.1 M of 1-ethyl-3-[3-dimethylaminopropyl]carbodiimide hydrochloride and similarly blocked was used as the background control. Between association and dissociation, the surface was washed with buffer for 180 seconds. The sensor surface was regenerated after each injection cycle to allow interaction between surface and fresh ligands for the next cycle. The binding of s100B was performed on the same immobilized chip. The sensorgrams were analyzed with BIAeval 3.1 software by global fitting using 1:1 Langmuir binding model (HMGB1) or steady state kinetic model (S100B). The kinetics data were calculated as $K_a$ (association rate), $K_d$ (dissociation rate) and $K_D$ ($K_D=K_d/K_a$). Both the background and blank injection (buffer without the ligand) were subtracted from recorded sensorgrams.

Results

The Majority of sRAGE$^{CHO}$ is Modified with the Complex Type of N-Glycans

In mutagenesis studies, it was determined that sRAGE$^{CHO}$ is glycosylated at the two putative N-glycosylation sites, N25 and N81 (FIG. 3). While it is known that insect cells generate pauci- or high-mannose-type N-glycans, mammalian cells may produce more diverse types of N-glycans including complex- and hybrid-type of N-glycans that cannot be produced in insect cells (Kamerling and Boons, *Comprehensive glycoscience: from chemistry to systems biology*, Elsevier, Amsterdam; Boston, 2007). To examine whether sRAGE$^{CHO}$ is modified differently than that of sRAGE$^{sf9}$, the migration of untreated and peptide-N-glycosidase F (PNGase F)-treated sRAGE produced from the two cell systems were compared on SDS-PAGE. The untreated sRAGE$^{sf9}$ migrated faster than that of sRAGE$^{CHO}$ (FIG. 5, lanes 1 and 2), whereas sRAGE from the two sources migrated similarly after PNGase F treatment, which removes the entire N-glycan (FIG. 5, lanes 7-10). These observations indicate that sRAGE produced from the two cell systems are indeed modified differently at their N-glycosylation sites.

Next, the carbohydrate composition of the N-glycan of sRAGE$^{CHO}$ was analyzed using high-performance anion-exchange chromatography (HPAEC). Complex-type glycans contain a 3-mannose (Man) core structure linked to a variable number of N-acetylglucosamine (GlcNAc), galactose (Gal), fucose (Fuc) and sialic acid (also termed N-acetylneuraminic acid, Neu5AC) residues, while high-mannose-type glycans have a 2-3-fold higher mannose content and no Gal, GlcNAc and sialic acid. Hybrid-type glycans have one Gal-GlcNAc sequence in one branch and variable numbers of Man on the other branch. The data (Table 2) suggests that sRAGE$^{CHO}$ may contain all three types of N-glycans. Resolving PNGase F-released N-glycans from sRAGE$^{CHO}$ with HPAEC and comparing their elution positions with standard glycan types, it was determined that approximately 70% of the total glycans are anionic species and the rest (~30%) are neutral species (FIG. 6A). Desialylation of N-glycans with mild acid almost completely eliminated anionic glycans and produced free Neu5Ac-linked N-glycan (FIG. 6B), suggesting that the majority of the observed anionic species from sRAGE$^{CHO}$ are sialylated glycans, and hence belong to the complex-type. Treatment of sRAGE$^{CHO}$ with neuraminidase, which removes sialic acids from the N-glycan, also affected its migration on SDS-PAGE (FIG. 5, lanes 3-6), confirming that the majority of sRAGE$^{CHO}$ are indeed sialylated.

TABLE 2

Carbohydrate composition of sRAGE$^{CHO}$

| | mol/mol protein |
|---|---|
| Fuc[a] | 0.9 |
| GlcNAc[b] | 6.6 |
| Gal[a] | 3.3 |
| Man[a] | 7.8 |
| Neu5Ac[c] | 1.1 |

[a] sRAGE$^{CHO}$ sample was hydrolyzed with 2M trifluoroacetic acid at 100° C. for 4 h
[b] sRAGE$^{CHO}$ sample was hydrolyzed with 4M HCl at 100° C. for 6 h
[c] sRAGE$^{CHO}$ sample was hydrolyzed with 20 mM HCl at 55° C. for 30 min GlcNAc was measured as N-acetylglucosamine after hydrolysis The presence of sialic acid in recombinant sRAGE produced in CHO-CD14 cells also was assessed by treatment with neuraminidase. To do so, approximately 15 µg sRAGE was incubated with 40 units of neuraminidase (New England Biolabs, Ipswich, Mass.) according to the manufacturer's instructions. At 0.5, 1, and 2 hour time points, a sample of the reaction mixture was obtained, and the reaction was terminated by adding lithium dodecyl sulfate sample buffer. Untreated sRAGE and each neuraminidase-treated sRAGE sample were resolved by SDS-PAGE and immunoblotted with anti-T7 antibodies.

The sRAGE present in each of the neuraminidase-treated sRAGE samples migrated faster than untreated sRAGE, indicating that neuraminidase treatment had released sialic acid from recombinant sRAGE produced in CHO-CD14 cells.

These results demonstrate the carbohydrate composition of recombinant sRAGE produced in CHO-CD14 cells and provide evidence that recombinant sRAGE produced in CHO-CD14 cells contains high levels of sialic acid species.

sRAGE$^{CHO}$ has a Higher Ligand Affinity to HMGB1

To test whether sRAGE modified with the complex-type of N-glycans has higher affinity to RAGE ligands, BIAcore™ surface plasmon resonance (SPR) studies were performed, using two RAGE ligands, HMGB1 and s100B, and four purified sRAGEs with different N-glycosylation status: sRAGE$^{CHO}$, sRAGE$^{sf9}$, desialylated sRAGE$^{CHO}$, and sRAGE$^{CHO}$ with N25T/N81T mutations that abolish N-glycosylation. The results showed that while all four sRAGEs binds s100B, sRAGE$^{CHO}$(N25T/N81T) has the highest affinity and sRAGE$^{CHO}$ has the lowest (Table 3, FIG. 7). In contrast, among the 4 tested sRAGEs, only sRAGE$^{CHO}$ binds HMGB1 ($K_D$=13.3±1.4 nM) in the experimental setting (Table 3, FIG. 7). These results indicate that HMGB1 may be the key injury-elicited RAGE ligand that enhances neointimal growth, and that sRAGE with complex-type of N-glycans specifically inhibits HMGB1.

TABLE 3

| Ligand binding affinity of sRAGE | | |
|---|---|---|
| | $K_D^a$ (HMGB1) | $K_D^b$ (S100B) |
| sRAGE$^{CHO}$ | 13.3 ± 1.4 nM | 90.5 nM |
| sRAGE$^{CHO}$(desialylation) | ND[c] | 25.3 nM |
| sRAGE$^{sf9}$ | ND[c] | 32.0 nM |
| sRAGE$^{CHO}$(N25T/N81T) | ND[c] | 13.6 nM |

Figure 8A:
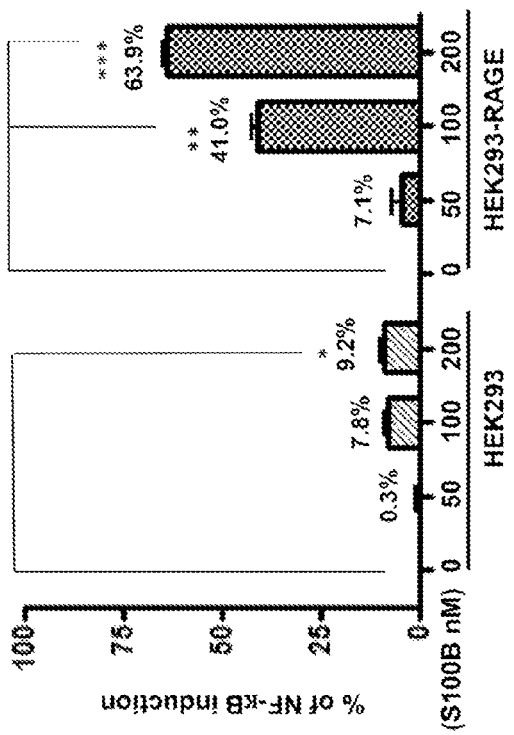
FIGS. 8A-8B are graphs showing that RAGE ligands HMGB1 and s100B activate NF-κB in the cell. RAGE ligand-induced NF-κB activity was measured with the Dual-Glo® luciferase assay system (Promega) according to the instruction of the manufacturer. Both HEK 293 and HEK 293 cells stably expressing RAGE were stimulated with RAGE ligands HMGB1 and S100B for 2 hours with the indicated concentrations. NF-κB-dependent luciferase activity was measured in the cell lysates.
Figure 8B:
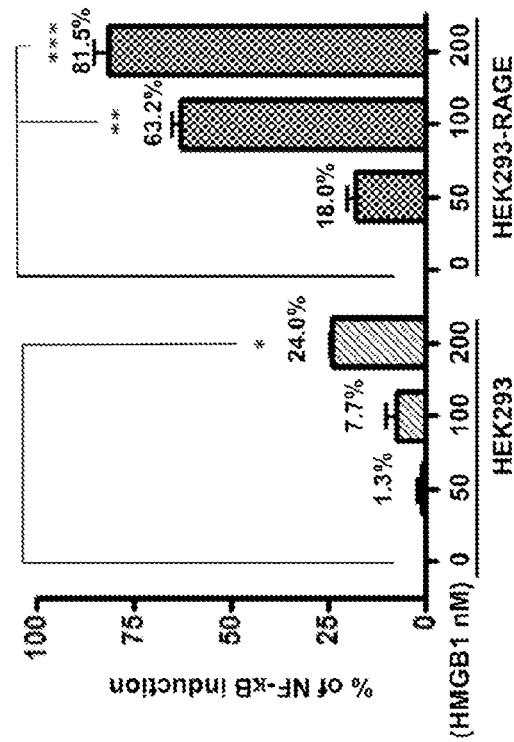
Figure 9A:
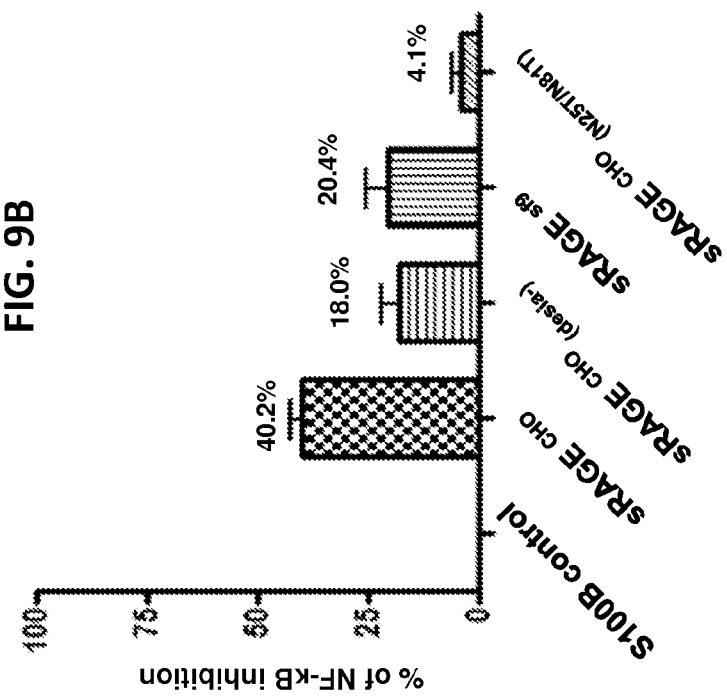
FIGS. 9A-9B are a pair of graphs showing NF-κB activation by RAGE ligands is inhibited by sRAGE. RAGE ligand (100 nM) and sRAGE (100 nM) were added to cells for 2 hours at 37° C. before lysis and luciferase assays.
Figure 9B:
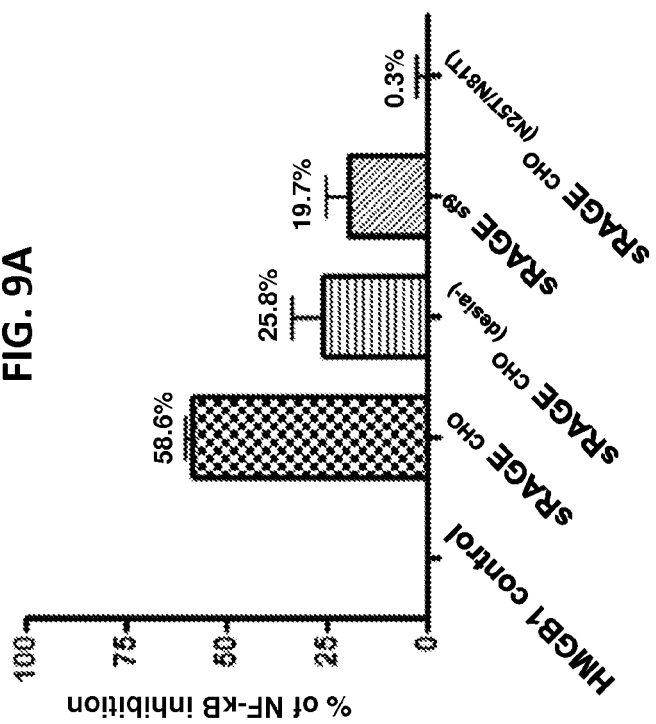
Figure 10A:
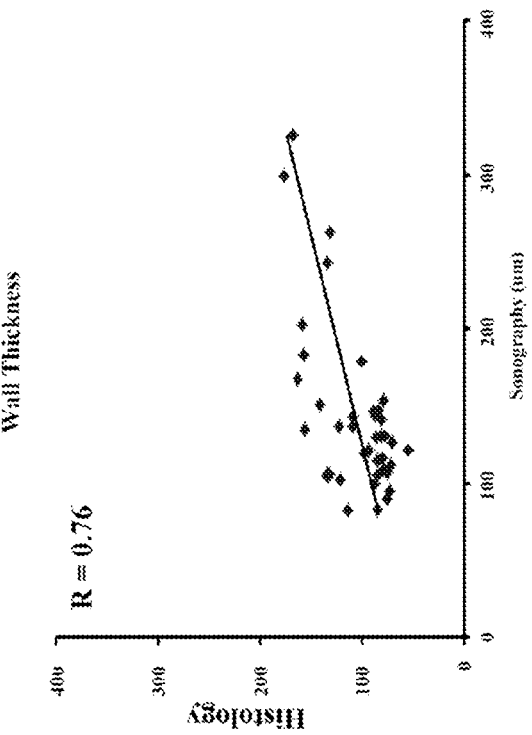
FIGS. 10A-10B are graphs showing correlation of histology and ultrasound sonography assessments of lumen diameter and wall thickness.
Figure 10B:
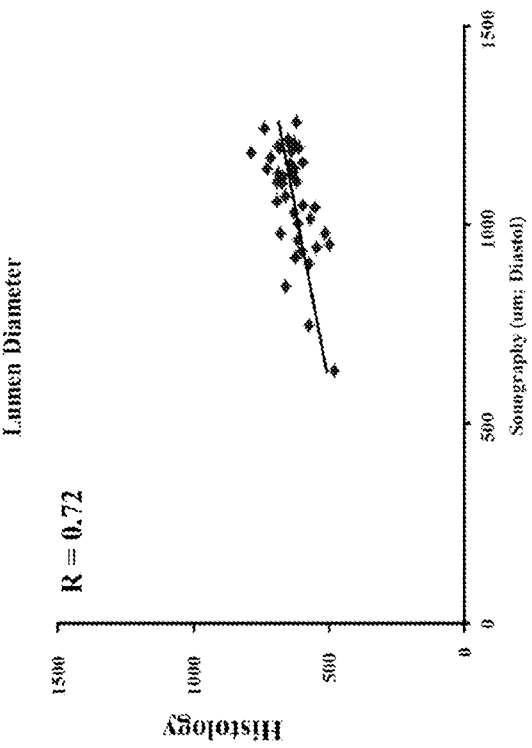

[a] $K_D$ calculated using 1:1 Langmuir model
[b] $K_D$ calculated using steady state model
[c] no binding NF-κB Inhibition by sRAGE is Associated with its N-Glycan Structure RAGE signaling activates the NF-κB transcription program in the cell, leading to inflammation. To test whether the N-glycan structure of sRAGE is indeed associated with its biopotency, the ability of differentially modified sRAGEs to inhibit NF-κB activation was studied using luciferase reporter assays. RAGE ligands HMGB1 and s100B specifically activate NF-κB in human embryonic kidney (HEK293) cells that stably express human RAGE (FIGS. 8A-8B). Adding sRAGE with the ligand dampens NF-κB activation, and the degree of inhibition is associated with the N-glycosylation status of sRAGE (FIGS. 9A and 9B): sRAGE$^{CHO}$ has the highest inhibitory potency (blocks 58.6% HMGB1-induced and 40.2% s100B-induced NF-κB activity respectively), whereas sRAGE$^{CHO}$(N25T/N81T) barely inhibits NF-κB (0.3% for HMGB1-induced and 4.1% for s100B-induced NF-κB activity, respectively). sRAGE$^{CHO}$(desialylated) and sRAGE$^{sf9}$ also blocks NF-κB activation but with reduced potency (25.8% and 19.7% for HMGB1-induced, and 18.0% and 20.4% for s100B-induced, respectively). Together, these results demonstrated that the higher potency of sRAGE$^{CHO}$ is associated with its N-glycan structure.

sRAGE$^{CHO}$ is Highly Potent and Effectively Blocks Neointimal Growth in a Rat Carotid Artery Balloon Injury Model Using a rat carotid artery balloon injury model, it was tested whether sRAGE$^{CHO}$ also potently inhibits neointimal growth in vivo. Low doses (0.125, 0.25 and 0.5 ng/g) of purified sRAGE$^{CHO}$ were administered via intraperitoneal injection to balloon-injured rats once 24 hours prior to balloon injury, once immediately after balloon injury and once 24 hours after balloon injury. Vessel ultrasound sonography was performed on live rats and histomorphological analysis on the vessel sections 2-week post-operation were employed to monitor the outcome (FIG. 10).

Figure 11A:
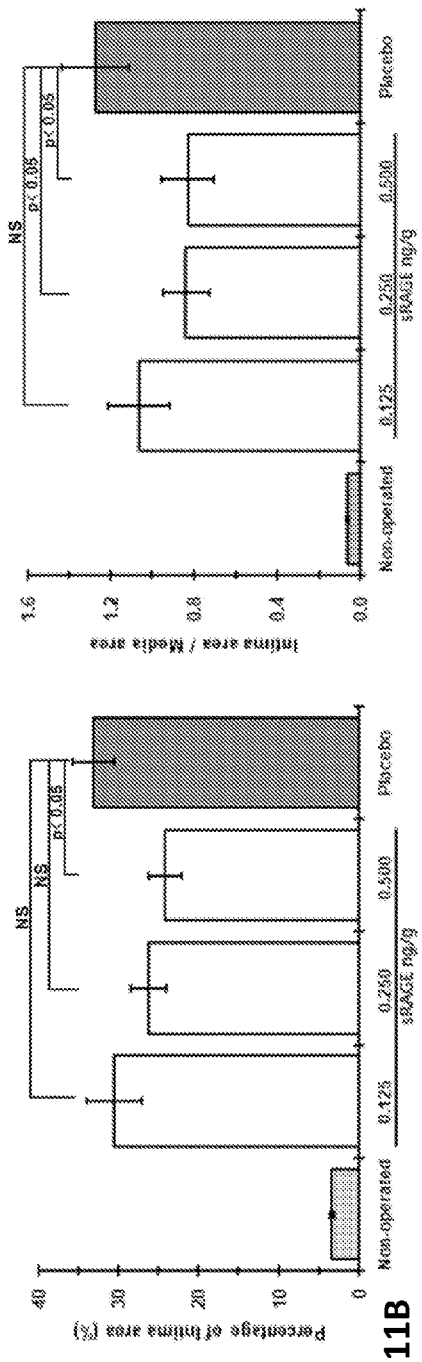
FIGS. 11A-11B are graphs showing that a low dose of sRAGE$^{CHO}$ sufficiently suppresses restenosis in rat carotid artery balloon injury models. Four groups of rats (n=8-10/group) were operated and administered sRAGE$^{CHO}$ or placebo.
Figure 11B:
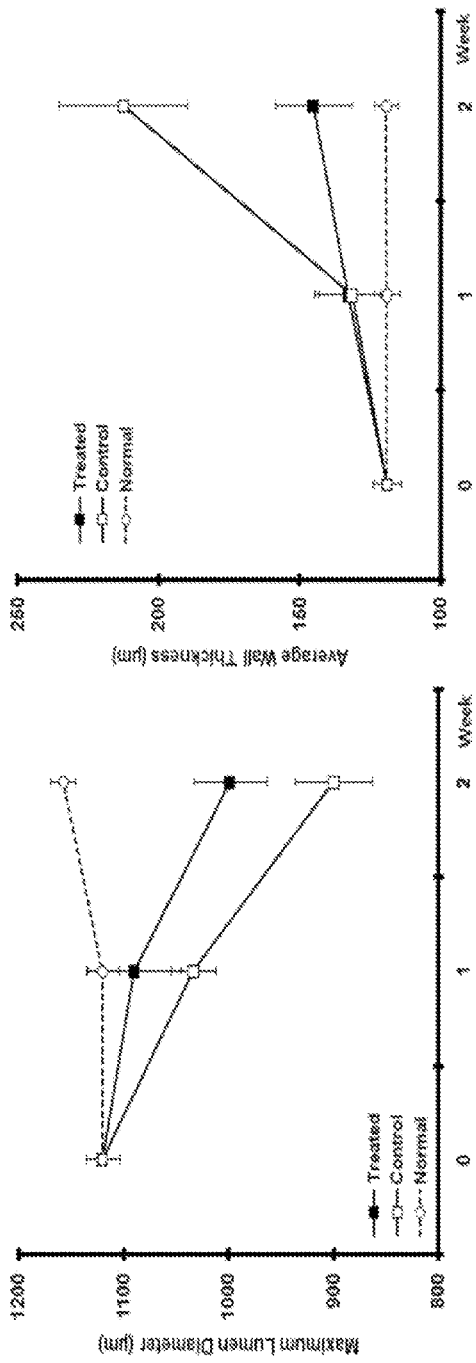
Figure 12:
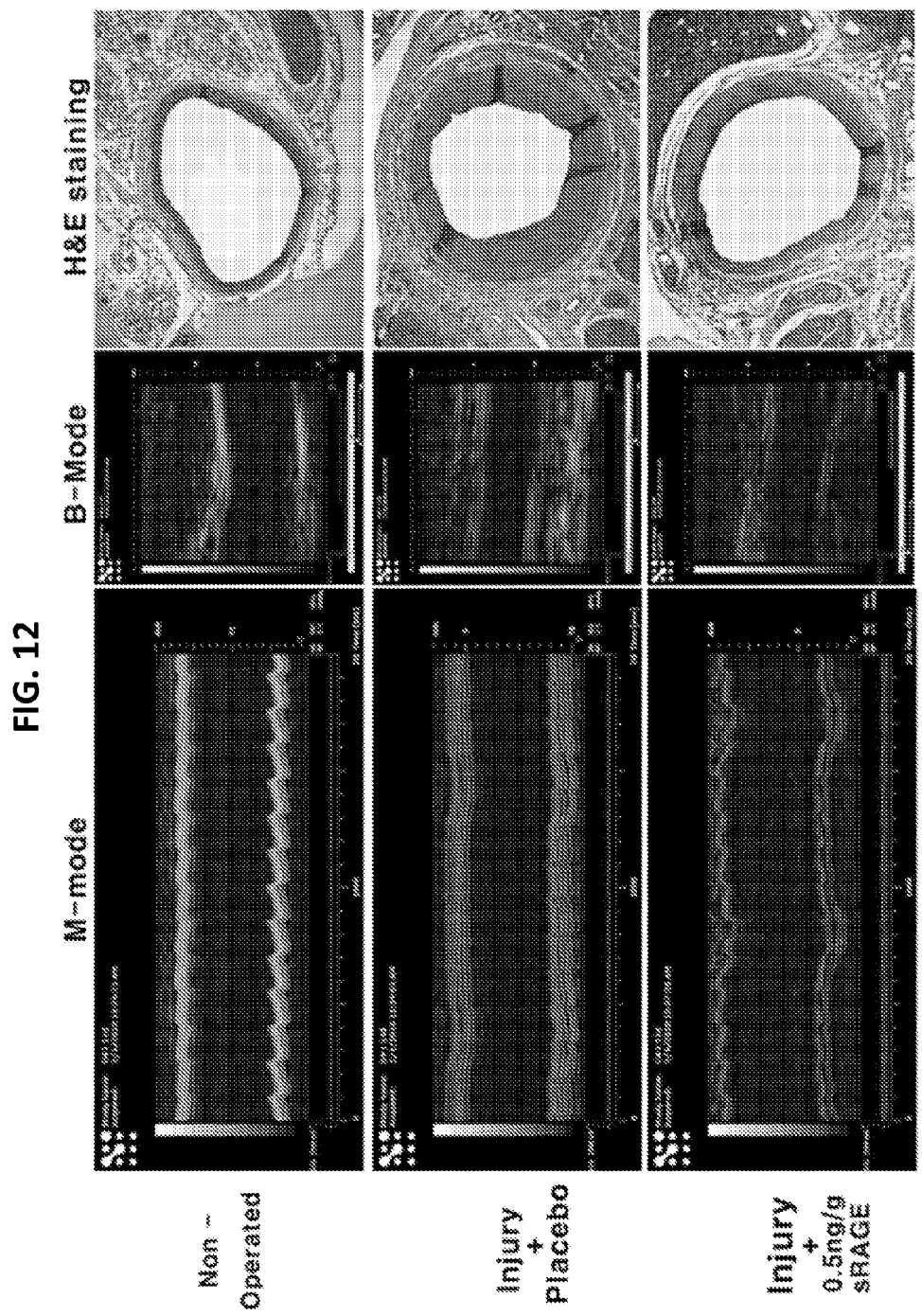
FIG. 12 shows representative vessel sonographic images (left and middle panels, 14 days post-injury) and the corresponding histological sections (right panels) from the same subjects. For sonography, M- and B-ultrasonic modes were recorded. The scale bar of stained vessels=100 μm.

At one week post-surgery, there was no detectable difference in maximum carotid artery lumen diameter or average carotid artery wall thickness as measured by ultrasound sonography between the injured left carotid artery of placebo-treated rats (FIG. 11B, "Control"), the uninjured right carotid artery of 0.5 ng/g-treated rats (FIG. 11B, "Normal"), and the injured left carotid artery of 0.5 ng/g-treated rats (FIG. 11B, "Treated"). However, at two weeks post-surgery, the maximum lumen diameter of the injured left carotid artery of 0.5 ng/g-treated rats was greater than the maximum lumen diameter of the injured left carotid artery of placebo-treated rats, and the average wall thickness of the injured left carotid artery of 0.5 ng/g-treated rats was less than the average wall thickness of the injured left carotid artery of placebo-treated rats (FIG. 11B). The maximum carotid artery lumen diameter and the average carotid artery wall thickness of the uninjured right carotid artery of 0.5 ng/g-treated rats did not change substantially over the course of the experiment. Representative carotid artery sonographic images at two weeks post-surgery are provided as FIG. 12.

The rats were euthanized two weeks post-surgery. Immediately following the sacrifice, the thoracic cavity was opened. Through an incision on the right ventricle, the vasculature was flushed with saline until clear, and then fixed with 10% neutral buffered formalin (NBF). The aorta and the carotid vessels were harvested, dissected free from the surrounding connective tissue, and further fixed in 10% NBF. Sections of the aorta and carotid vessels (2-3 mm in length) were prepared from the aortic-arch to bifurcation region (internal and external carotid artery), processed, embedded in paraffin, cut into 7 μm cross-sections, and stained with hematoxylin and eosin (H&E). Morphological analyses of the carotid artery segments were performed with a digital imaging analysis system (MCID, GE Healthcare, Piscataway, N.J.).

As expected, there was an increase in the intimal area and the intima/media area ratio in the carotid arteries of all injured carotid arteries as compared to non-operated carotid arteries, as assessed by morphological analyses of H&E-stained sections (FIG. 11A). There was a slight decrease in the intimal area and the intima/media area ratio in the injured left carotid artery of 0.125 ng/g- and 0.25 ng/g-treated rats as compared to the injured left carotid artery of placebo-treated rats (FIG. 11A). Moreover, there was a statistically significant decrease in the intimal area and the intima/media area ratio in the injured left carotid artery of 0.5 ng/g-treated rats as compared to the injured left carotid artery of placebo-treated rats (FIG. 11A). Representative H&E-stained carotid artery sections are provided as FIG. 12.

cient to elicit a therapeutic response in a rat vascular balloon injury model, which dose is significantly reduced as compared to the typical 100 μg/day/mouse dose of non-mammalian-expressed sRAGE previously reported (see, e.g., Bucciarelli et al., *Circulation* 106: 2827-2835, 2002; Harja et al., *J. Clin. Invest.* 118: 183-194, 2008; Park et al., *Nat. Med.* 4: 1025-1031, 1998; Sakaguchi et al., *J. Clin. Invest.* 111: 959-972, 2003; Tanaka et al., *J. Biol. Chem.* 275: 25781-25790, 2000; Zhang et al., *Am. J. Respir. Crit. Care Med.* 178: 356-362, 2008; and Zhou et al., *Circulation* 107: 2238-2243, 2003).

Figure 13:
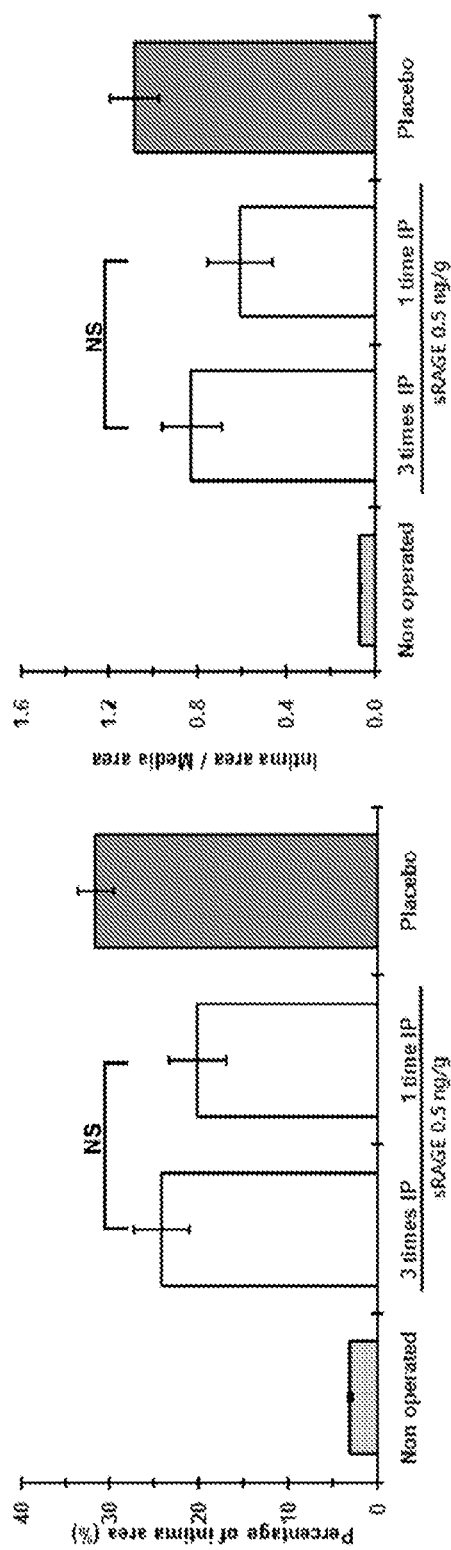
FIG. 13 is a graphical depiction of the effects of the administration of 0.5 ng/g sRAGE produced in mammalian cells on neointima hyperplasia when administered one time immediately after balloon injury, or three times (24 hours prior to injury, immediately after injury, and 24 hours after injury) as determined by histomorphological analyses of carotid artery sections harvested 2 weeks post-balloon injury. The percentage of neointima area in the vessel wall (left) and the I/M ratio (right) are shown. The error bars represent means±SEM, (n=8-10). NS: not significant. The results show that a single bolus administration is as effective as three injections.

Because acute injury often triggers "danger signals" including an immediate release of RAGE ligands such as alarmins (Palumbo et al., *J Cell Biol* 164:441-449, 2004; Tsung et al., *J Exp Med* 201:1135-1143, 2005), it was reasoned that scavenging these ligands at an early stage of injury may offset RAGE signaling cascades and dampen the subsequent inflammation and maladaptation. To test this hypothesis, a single bolus of sRAGE$^{CHO}$ (0.5 ng/g) was intraperitoneally injected to rats immediately after the surgery, and the histomorphological results were compared to rat groups that received 3 injections. The results (FIG. 13) showed that there is no statistical difference in outcomes between the rat group that received 3 injections and those that received single bolus, indicating that a single administration of sRAGE$^{CHO}$ immediately after the surgery is just as effective as multiple doses.

Figure 14A:
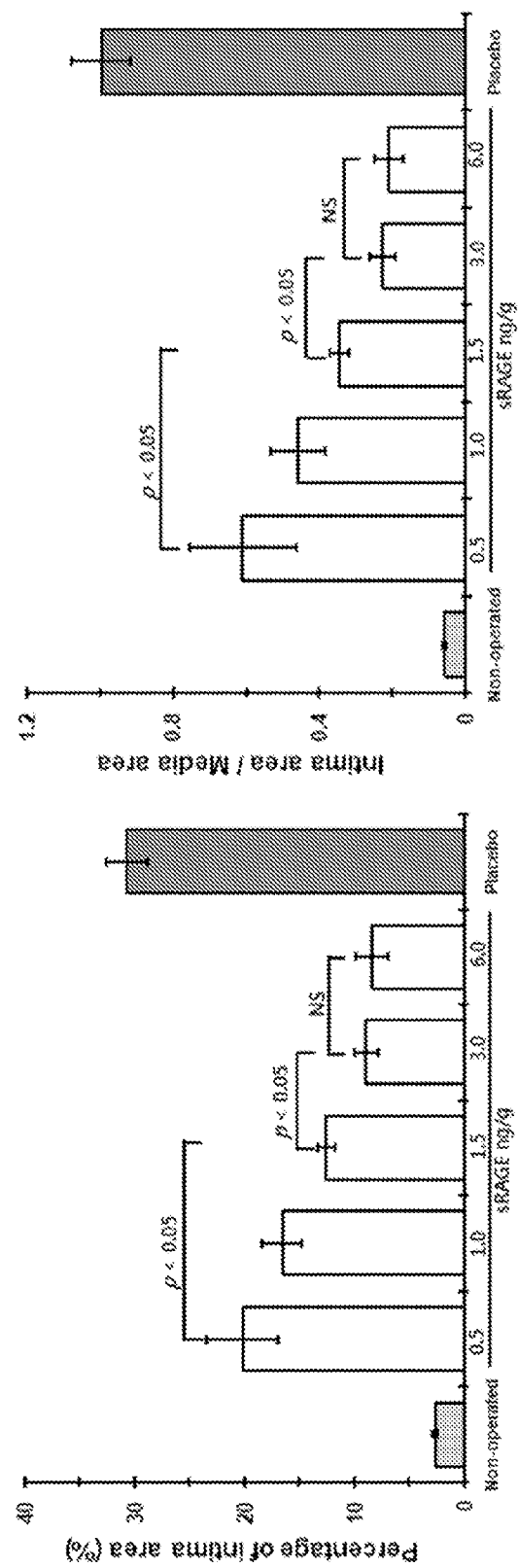
FIG. 14A is a graphical depiction of the effects of a single bolus of sRAGE at doses of 0.5, 1, 1.5, 3, and 6 ng/g administered immediately after balloon injury as determined by histomorphological analyses of carotid artery sections harvested 2 weeks post-balloon injury. The percentage of neointima area in the vessel wall (left) and the I/M ratio (right) are shown. The error bars are means±SEM (n=8-10).
Figure 14B:
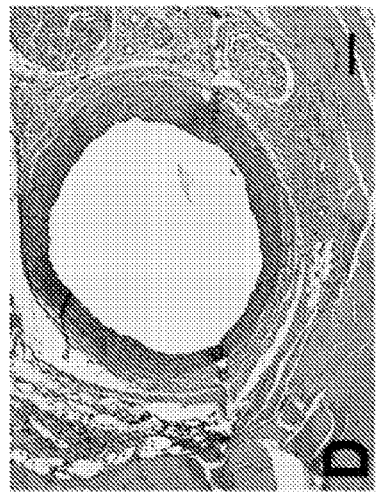
FIGS. 14B-14G includes photomicrographs of representative H&E-stained sections of the placebo group and the 0.5, 1.0, 1.5, 3.0, and 6.0 ng/g sRAGE dose groups, respectively.
Figure 14C:
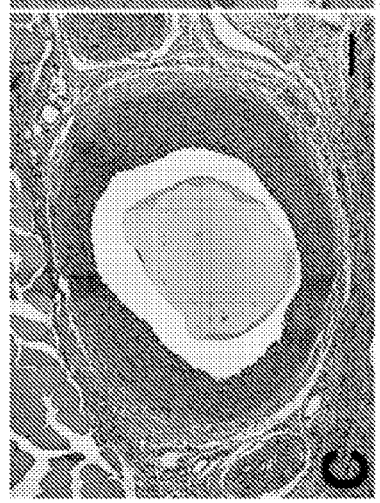
Figure 14D:
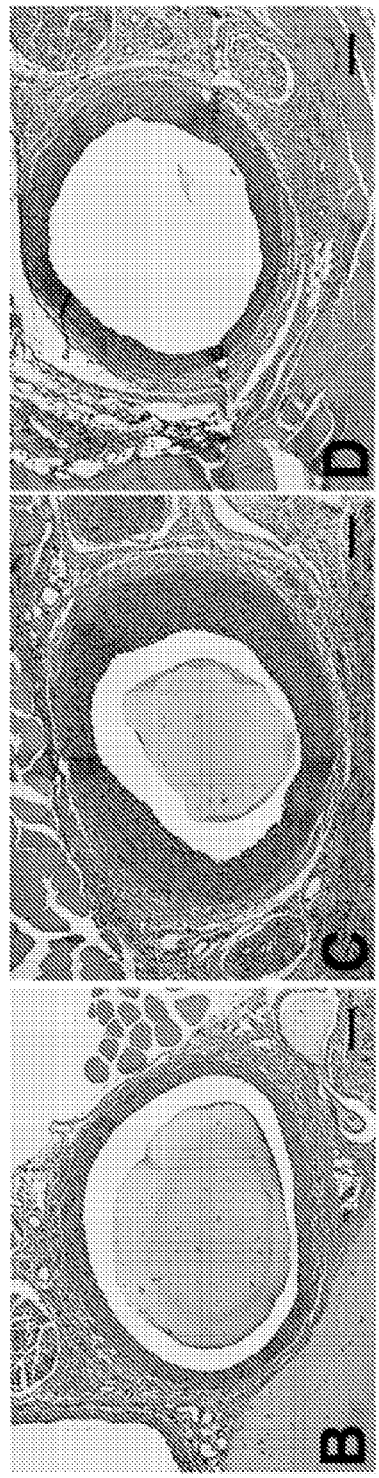
Figure 14E:
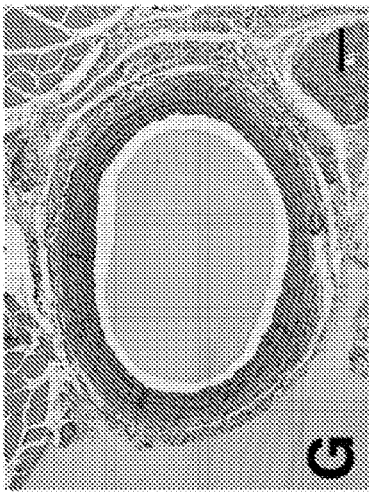
Figure 14F:
Figure 14G:

The effective therapeutic dose of sRAGE$^{CHO}$ was next determined using a single dose injection. Five doses were tested (0.5, 1.0, 1.5, 3.0, and 6.0 ng/g body weight). Two weeks post-surgery, the rats were euthanized, and H&E-stained sections of the carotid arteries were prepared. Morphological analyses of the H&E-stained sections demonstrated attenuation of the intima area and intima/media area ratio in the injured carotid arteries in all sRAGE-treated rats as compared to placebo-treated rats (FIG. 14A). Moreover, the effect of sRAGE on the attenuation of the intima area and intima/media area ratio in the injured carotid arteries was dose dependent (FIG. 14A). Representative H&E-stained sections of the placebo group and the 0.5, 1.0, 1.5, 3.0, and 6.0 ng/g sRAGE dose groups are provided as FIGS. 14B-14G, respectively.

To evaluate whether sRAGE treatment affected the overall health of the rats, whole body and major organ weights were determined at sacrifice. No pathological changes were observed in the major organs examined. In addition, treatment with sRAGE did not lead to any significant differences in body weight or in the weight of any major organ examined (see Table 4).

TABLE 4

| | Placebo[a] | sRAGE treatment[a] | | | | |
| --- | --- | --- | --- | --- | --- | --- |
| | | 0.5 ng/g | 1.0 ng/g | 1.5 ng/g | 3.0 ng/g | 6.0 ng/g |
| Body weight | 459.04 ± 9.09 | 443.53 ± 16.15 | 472.19 ± 11.72 | 461.77 ± 8.21 | 461.57 ± 14.78 | 473.15 ± 9.79 |
| Heart/BW[b] | 0.31 ± 0.01 | 0.33 ± 0.01 | 0.33 ± 0.01 | 0.30 ± 0.01 | 0.30 ± 0.01 | 0.28 ± 0.01 |
| Liver/BW[b] | 3.83 ± 0.08 | 3.68 ± 0.12 | 3.69 ± 0.08 | 3.76 ± 0.09 | 3.95 ± 0.10 | 3.78 ± 0.14 |
| Kidney/BW[b] | 0.41 ± 0.01 | 0.43 ± 0.02 | 0.42 ± 0.01 | 0.41 ± 0.01 | 0.39 ± 0.01 | 0.38 ± 0.01 |
| Spleen/BW[b] | 0.22 ± 0.01 | 0.22 ± 0.01 | 0.21 ± 0.01 | 0.22 ± 0.01 | 0.23 ± 0.01 | 0.23 ± 0.01 |
| Lung/BW[b] | 0.55 ± 0.02 | 0.58 ± 0.04 | 0.56 ± 0.03 | 0.53 ± 0.03 | 0.44 ± 0.02 | 0.46 ± 0.02 |
| Thymus/BW[b] | 0.12 ± 0.01 | 0.12 ± 0.01 | 0.11 ± 0.01 | 0.11 ± 0.01 | 0.12 ± 0.01 | 0.13 ± 0.01 |
| Testis/BW[b] | 0.40 ± 0.01 | 0.42 ± 0.01 | 0.39 ± 0.01 | 0.41 ± 0.01 | 0.41 ± 0.01 | 0.38 ± 0.01 |

[a]Mean ± SEM, n = 8-10 for each treatment or placebo group;
[b]Organ/body weight (BW)

Figure 15:
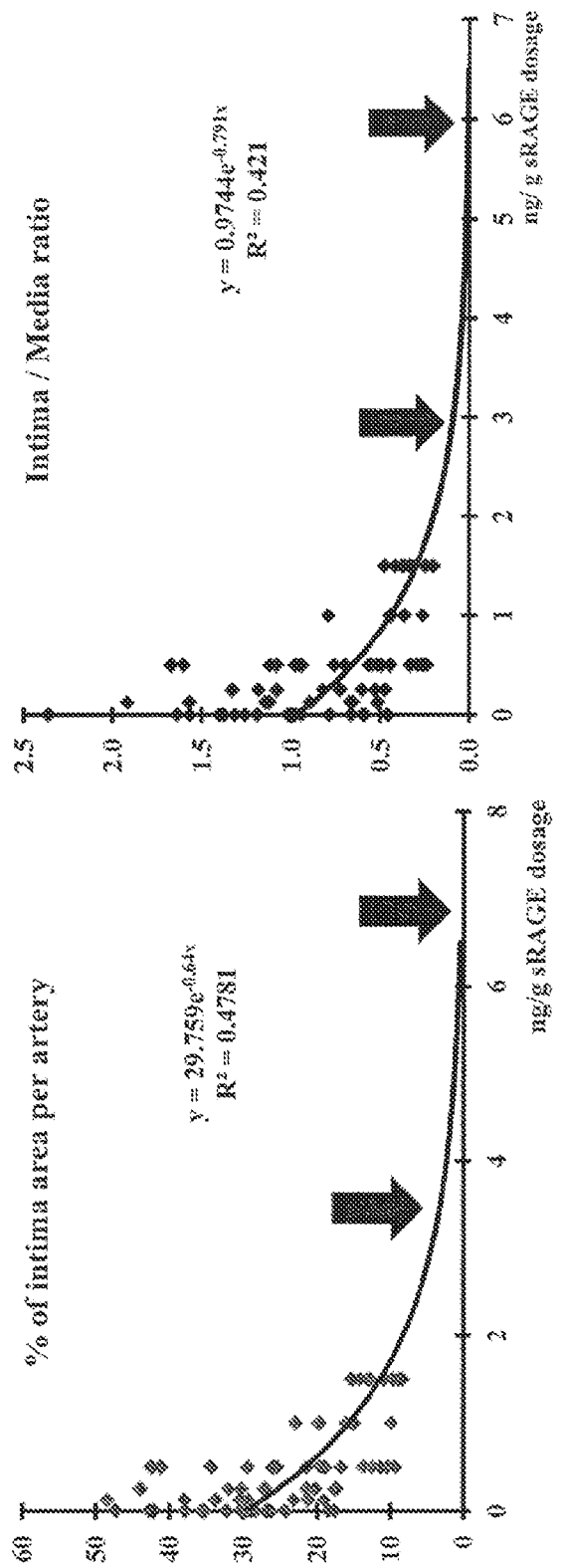
FIG. 15 is a pair of graphs depicting regression analyses performed to estimate the maximal effective dose of human sRAGE produced in mammalian cells based on percentage of intima area (left) and the intima/media ratio (right) in carotid artery sections harvested 2 weeks post-balloon injury.
Figure 16A:
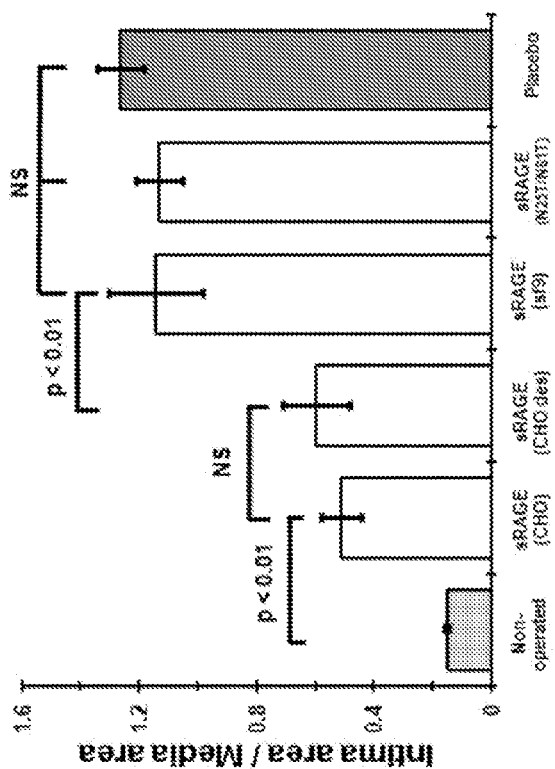
FIGS. 16A-16H show N-glycosylation of sRAGE contributes to its high therapeutic potency. A single dose of 3 ng/g sRAGE$^{CHO}$, sRAGE$^{CHO}$(desialylation), sRAGE$^{sf9}$, and sRAGE$^{CHO}$ (N25T/N81T) was injected to rat groups (n=8-12) immediately after surgery, and histomorphological analysis on vessel sections were performed 2-week post-surgery.
Figure 16B:
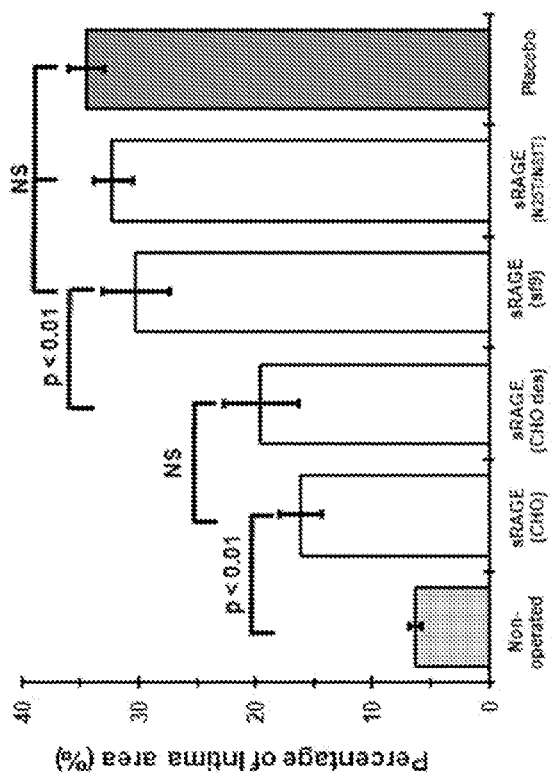
Figure 16C:
Figure 16D:
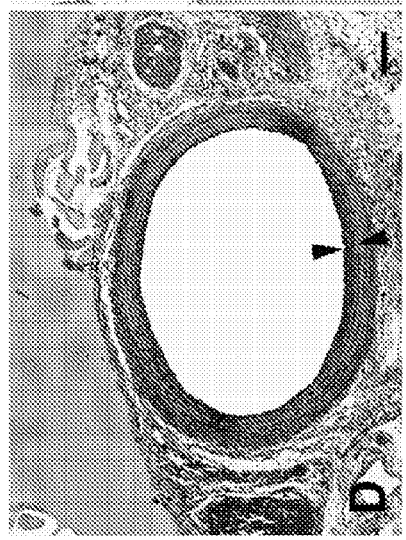
Figure 16E:
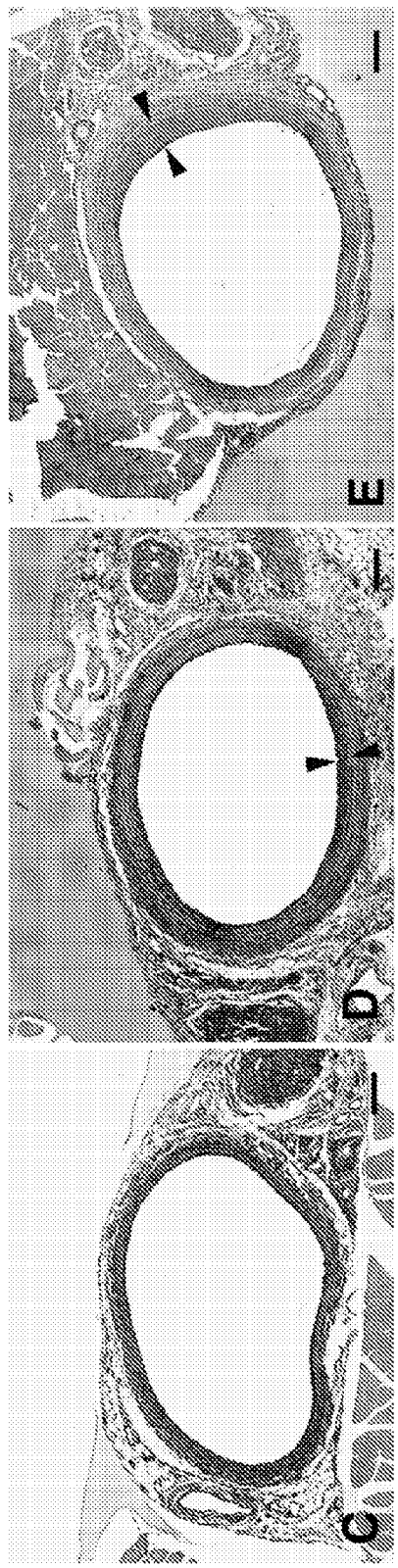
Figure 16F:
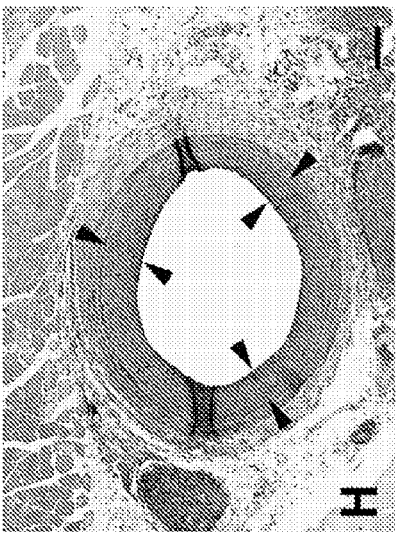
Figure 16G:
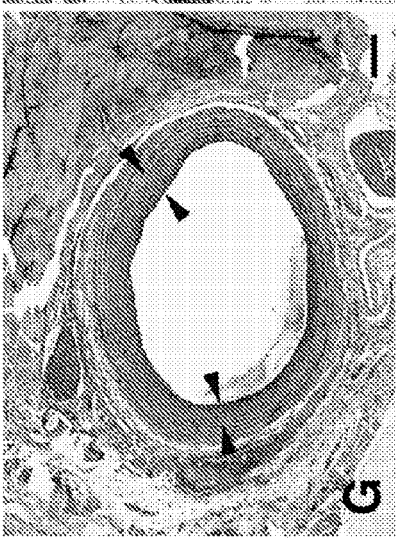
Figure 16H:
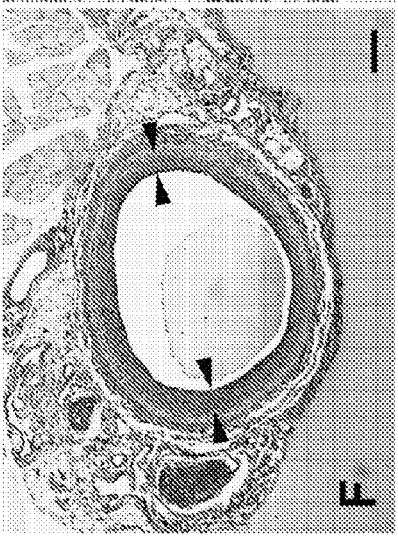

The results of this example demonstrate that a dose of 0.5 ng/g body weight of recombinant human sRAGE produced according to the methods of the present disclosure is suffi- Regression analyses were then performed to determine the sRAGE dose that can maximize the suppression of neointima expansion. Based upon the data described in FIG. 14, linear regression analyses predicted the maximal effective sRAGE dose to be 3-6 ng/g body weight (FIG. 15). However, while the 3 ng/g dose showed improved suppression compared to the lower doses, the 6 ng/g dose exhibited similar effects to those of the 3 ng/g dose (FIG. 14A). These findings suggest that a dose higher than 6 ng/g may not have additional beneficial effects.

The effect of sRAGE on neointima formation in balloon-injured carotid arteries also was assessed by calculating the treatment effect on the reduction of intima area and the reduction of the intima/media area ratio, the results of which are shown in Table 5.

TABLE 5

Effects of sRAGE$^{CHO}$ dose in vessels of balloon-injured rats

| sRAGE dose (ng/g) | Intima area (μm²) | Reduced intima area (%)$^a$ | Intima/ media | Reduced intima/media (%)$^b$ |
|---|---|---|---|---|
| Placebo | 120,204.15 | 0 | 1.08 | 0 |
| 0.5 | 66417.22 | 35.8 | 0.61 | 43.3 |
| 1.0 | 52827.58 | 47.3 | 0.45 | 58.2 |
| 1.5 | 37672.84 | 60.2 | 0.34 | 68.3 |
| 3.0 | 22850.26 | 71.6 | 0.23 | 78.8 |
| 6.0 | 20889.66 | 73.2 | 0.20 | 81.4 |

$^a$reduction of intima area was calculated as:

$$\frac{\text{Intima area of placebo-treated vessel} - \text{intima area of sRAGE}^{CHO}\text{-treated vessel}}{\text{Intima area of placebo-treated vessel}} \times 100\%$$

$^b$reduction of intima/media ratio was calculated as:

$$\frac{\text{I/M of placebo-treated vessel} - \text{I/M of sRAGE}^{CHO}\text{-treated vessel}}{\text{I/M of placebo-treated vessel}} \times 100\%$$

The results of this example demonstrate that a single bolus of recombinant human sRAGE produced in mammalian cells suppresses neointima formation when administered in an amount as low as 0.5 ng/g. The results further indicate that recombinant human sRAGE produced in mammalian cells displays a dose-dependent suppression of neointima formation when administered as a single bolus in the range of 0.5 ng/g-3 ng/g.

Inhibition of Neointimal Growth by sRAGE is Associated with its N-Glycan Profile Because sRAGE$^{CHO}$ and sRAGE$^{sf9}$ showed similar pharmacokinetics (FIG. 2), to directly compare the in vivo potency of sRAGEs with different N-glycan profiles, a single dose of 3 ng/g of each sRAGE preparations was injected into rats immediately after carotid artery balloon injury procedure. Compared to placebo, the suppression of neointimal growth by sRAGE$^{CHO}$(N25T/N81T) and sRAGE$^{sf9}$ is insignificant (FIGS. 16A, 16B, 16F and 16G). On the other hand, the suppression of neointimal growth by sRAGE$^{CHO}$(desialylation), although slightly less potent, is not statistically different from that of sRAGE$^{CHO}$ (FIGS. 16A, 16B, 16D and 16E). These results suggest that the N-glycans of sRAGE are indeed associated with its biopotency, and that although sialic acids at the termini of the N-glycan branches contribute to sRAGE bioactivity, the main structure of N-glycan is sufficient for blocking neointimal growth in this acute model.

Assessment of Inflammatory Markers in sRAGE$^{CHO}$-Treated Vessels

Figure 17A:
FIGS. 17A-17E show photomicrographs of carotid artery sections obtained from rats treated once with 3 ng/g sRAGE (left column) or placebo (center column), and stained for intracellular adhesion molecule (ICAM)-1 (FIG. 17A), vascular cell adhesion molecule (VCAM)-1 (FIG. 17B), RAGE (FIG. 17C), high mobility group box 1 (HMGB1) (FIG. 17D), or s100 (FIG. 17E) by immunohistochemistry. Also shown are graphical depictions (right column) of the assessment of the expression level of each inflammatory marker in the carotid artery sections (n=8-10, **$p<0.05$).
Figure 17B:
Figure 17C:
Figure 17D:
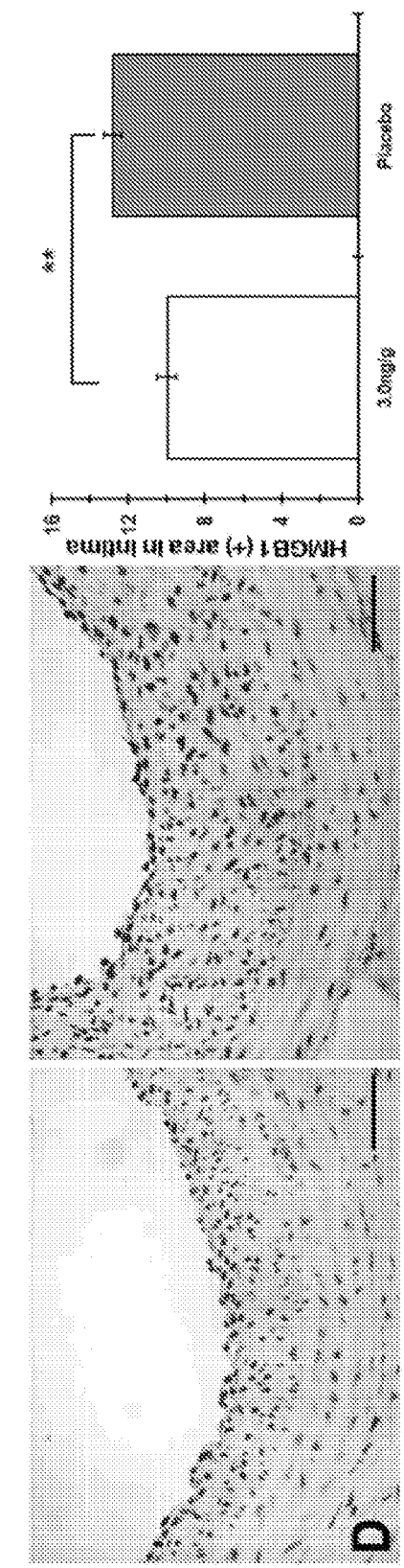
Figure 17E:
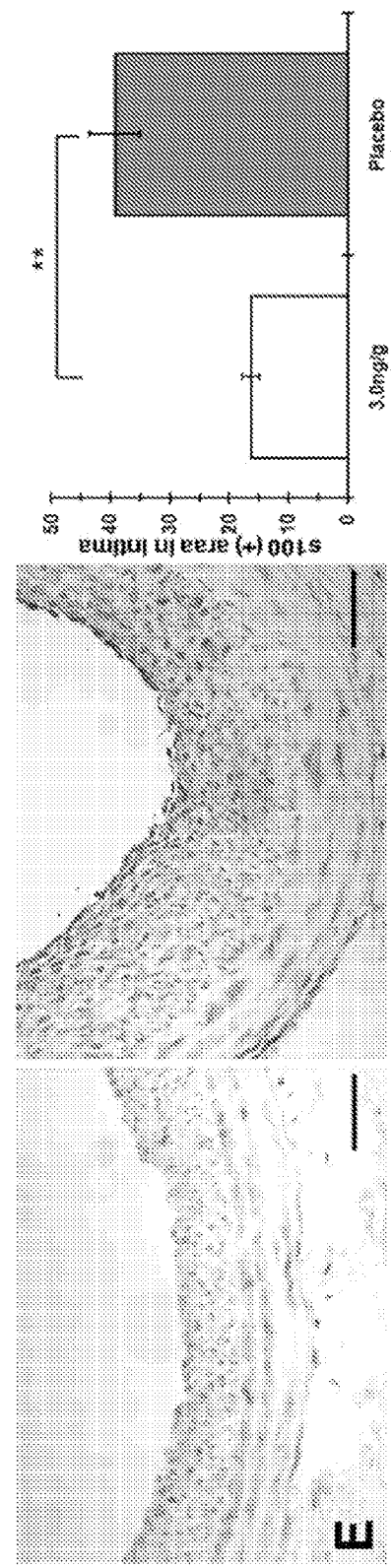

Previous studies showed that sRAGE$^{sf9}$ blocks neointimal expansion by scavenging RAGE ligands, attenuates vascular inflammation and restricts RAGE expression on the cell surface (Sakaguchi et al., *J Clin Invest* 111:959-972, 2003). Next, it was tested whether sRAGE$^{CHO}$ also attenuates vascular inflammation by assessing the expression of inflammatory markers, ICAM-1 and VCAM-1, as well as RAGE, on sRAGE$^{CHO}$ (3 ng/g) and placebo-treated vessel sections via immunohistochemistry (FIGS. 17A-17C). Compared to the placebo group, the sRAGE$^{CHO}$-treated group had significantly reduced expression of these markers, suggesting a down-regulated inflammatory signaling and monocyte adhesion. The expression of RAGE ligands HMGB1 and S100, known to be associated with cell necrosis and injuries (Bianchi, *J Leukoc Biol* 81:1-5, 2007; Korfias et al., *Curr Med Chem* 13:3719-3731, 2006; Zhu et al., *Inflamm Allergy Drug Targets* 9:60-72, 2010), was also examined on the vessel sections. As shown in FIGS. 17D and 17E, the sRAGE$^{CHO}$-treated vessel group had reduced HMGB1 and s100-staining on the neointima region compared to the placebo group, suggesting that sRAGE$^{CHO}$ blocks inflammation in the vessel.

These results demonstrate that mammalian-expressed sRAGE suppresses neointima expansion through attenuating inflammation (i.e., reducing ICAM-1 and VCAM-1) and through attenuating RAGE/ligand expression in the vasculature (i.e., reducing HMGB1 and S100).

EXAMPLE 5

This example demonstrates that hsRAGE expression is enhanced by GeneArt re-engineering.

The GeneArt platform was used to redesign the sRAGE sequence to enhance its expression. The nucleotide sequence of human, codon-optimized (for *Cricetulus griseus*) T7-sRAGE is set forth herein as SEQ ID NO: 12. To evaluate expression of the GeneArt re-engineered T7-sRAGE, CHO cells were transfected with either native human sRAGE cDNA or GeneArt-reengineered sRAGE cDNA. As shown in FIG. 18, significantly more sRAGE protein was detected by Western blot when cells were transfected with the GeneArt-reengineered construct, relative to cells transfected with the native cDNA construct.

These results demonstrate that expression of hsRAGE protein is enhanced using a GeneArt-reengineered cDNA sequence.

EXAMPLE 6

This example demonstrates that sRAGE$^{CHO}$ blocks acute ischemic myocardial infarction in rat acute coronary artery ligation models.

The cardioprotective effect of sRAGE$^{CHO}$ was evaluated in an acute coronary artery ligation model in rats. sRAGE$^{CHO}$ (1 μg/kg) was injected i.p. into rats immediately after left coronary artery ligation, and myocardial infarction (MI) size was assessed 24 hours after ligation by Evans Blue and TIC ((2, 3,5-triphenyltetrazolium chloride) staining. The percentage of AAR (area at risk), and MI within the AAR were assessed. As shown in FIG. 19, sRAGE$^{CHO}$-treated and control animals exhibited a similar percentage of AAR; however, the percentage of MI within the AAR was significantly lower in sRAGE$^{CHO}$-treated animals, relative to controls.

This data demonstrates that treatment with sRAGE$^{CHO}$ significantly reduces acute ischemic myocardial infarction in an animal model.

EXAMPLE 7

This prophetic example demonstrates the preparation of a composition comprising mammalian-expressed sRAGE suitable for single dose or long-term, repeated administration.

Tagged and untagged sRAGE are prepared as described in Examples 1 and 4, respectively. Tagged and untagged sRAGE are formulated separately into a pharmaceutically acceptable carrier such as saline solution, and administered to test animals following balloon injury to the carotid artery as described, for example, in Example 5, at an appropriate dose, such as 0.5-3 ng/g body weight. Animals are administered one or more intraperitoneal or intravenous injections of the untagged sRAGE (e.g., 1, 2, 3, 4, 5, 6, 7, 8, 9, or 10 injections, or more than 10 injections) at suitable time intervals, with appropriate controls including administration of saline alone and administration of T7-sRAGE. Efficacy of the sRAGE treatment is monitored by histomorphometric analyses, immunohistology, and/or ultrasound measurements. At appropriate intervals, samples are taken from the test animals and analyzed, such as by ELISA, to determine whether the animal has elicited an antibody reaction. Results are compared.

The results will show that untagged sRAGE is less immunogenic than T7-sRAGE after multiple administrations, and that untagged sRAGE has similar or improved efficacy as compared to T7-sRAGE.

In view of the many possible embodiments to which the principles of the disclosed present disclosure may be applied, it should be recognized that the illustrated embodiments are only preferred examples of the present disclosure and should not be taken as limiting the scope of the present disclosure. Rather, the scope of the present disclosure is defined by the following claims. We therefore claim as our present disclosure all that comes within the scope and spirit of these claims.

The invention claimed is:

1. A method of treating a vascular disease, vascular injury or vascular inflammation in a mammal, comprising administering to the mammal an isolated human soluble receptor for advanced glycation end products (sRAGE) polypeptide comprising a mammalian post-translation modification, wherein the amino acid sequence of the sRAGE polypeptide is at least 95% identical to SEQ ID NO: 4 and the mammalian post-translation modification comprises mammalian N-glycosylation, thereby treating the vascular disease, vascular injury, or vascular inflammation in the mammal.

2. The method of claim 1, further comprising a modification selected from the group consisting of phosphorylation, mammalian sulfation, mammalian carboxylation, mammalian hydroxylation, mammalian acetylation, mammalian myristoylation, mammalian farnesylation, mammalian ADP ribosylation, mammalian disulfide formation, and mammalian SUMOylation.

3. The method of claim 1, wherein the sRAGE polypeptide comprises a mammalian N-glycan profile.

4. The method of claim 1, wherein the mammal has a vascular disease, and the vascular disease comprises atherosclerosis or restenosis.

5. The method of claim 1, wherein the mammal has a vascular injury, and the vascular injury comprises acute myocardial infarction, angioplasty or traumatic injury.

6. The method of claim 1, wherein the mammal has vascular inflammation.

7. The method of claim 1, wherein the sRAGE polypeptide is administered within about 1 hour after a vascular injury.

8. The method of claim 1, wherein the sRAGE polypeptide is administered immediately after a vascular injury.

9. The method of claim 1, wherein the sRAGE polypeptide is administered in a single bolus to the mammal.

10. The method of claim 1, wherein the sRAGE polypeptide is administered to the mammal at a dose of about 0.5-10, about 1.5-6, or about 2-4 ng per gram body weight of the mammal.

11. The method of claim 1, wherein the mammal is a human.

12. The method of claim 1, wherein the amino acid sequence of the sRAGE polypeptide comprises or consists of SEQ ID NO: 4.

* * * * *

```
                        SEQUENCE LISTING

<160> NUMBER OF SEQ ID NOS: 12

<210> SEQ ID NO 1
<211> LENGTH: 404
<212> TYPE: PRT
<213> ORGANISM: Homo sapiens

<400> SEQUENCE: 1

Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
        35                  40                  45

Leu Glu Trp Lys Leu Asn Thr Gly Arg Thr Glu Ala Trp Lys Val Leu
    50                  55                  60

Ser Pro Gln Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
                85                  90                  95

Phe Arg Cys Gln Ala Met Asn Arg Asn Gly Lys Glu Thr Lys Ser Asn
            100                 105                 110

Tyr Arg Val Arg Val Tyr Gln Ile Pro Gly Lys Pro Glu Ile Val Asp
        115                 120                 125

Ser Ala Ser Glu Leu Thr Ala Gly Val Pro Asn Lys Val Gly Thr Cys
    130                 135                 140

Val Ser Glu Gly Ser Tyr Pro Ala Gly Thr Leu Ser Trp His Leu Asp
145                 150                 155                 160

Gly Lys Pro Leu Val Pro Asn Glu Lys Gly Val Ser Val Lys Glu Gln
                165                 170                 175

Thr Arg Arg His Pro Glu Thr Gly Leu Phe Thr Leu Gln Ser Glu Leu
            180                 185                 190

Met Val Thr Pro Ala Arg Gly Gly Asp Pro Arg Pro Thr Phe Ser Cys
        195                 200                 205

Ser Phe Ser Pro Gly Leu Pro Arg His Arg Ala Leu Arg Thr Ala Pro
    210                 215                 220

Ile Gln Pro Arg Val Trp Glu Pro Val Pro Leu Glu Glu Val Gln Leu
225                 230                 235                 240

Val Val Glu Pro Glu Gly Gly Ala Val Ala Pro Gly Gly Thr Val Thr
                245                 250                 255

Leu Thr Cys Glu Val Pro Ala Gln Pro Ser Pro Gln Ile His Trp Met
```

```
                    260               265                270
Lys Asp Gly Val Pro Leu Pro Leu Pro Pro Ser Pro Val Leu Ile Leu
            275                 280             285

Pro Glu Ile Gly Pro Gln Asp Gln Gly Thr Tyr Ser Cys Val Ala Thr
        290                 295             300

His Ser Ser His Gly Pro Gln Glu Ser Arg Ala Val Ser Ile Ser Ile
305             310                 315                 320

Ile Glu Pro Gly Glu Glu Gly Pro Thr Ala Gly Ser Val Gly Gly Ser
                325                 330                 335

Gly Leu Gly Thr Leu Ala Leu Ala Leu Gly Ile Leu Gly Leu Gly
            340                 345                 350

Thr Ala Ala Leu Leu Ile Gly Val Ile Leu Trp Gln Arg Arg Gln Arg
            355                 360             365

Arg Gly Glu Glu Arg Lys Ala Pro Glu Asn Gln Glu Glu Glu Glu Glu
        370                 375             380

Arg Ala Glu Leu Asn Gln Ser Glu Glu Pro Glu Ala Gly Glu Ser Ser
385             390                 395                 400

Thr Gly Gly Pro
```

<210> SEQ ID NO 2
<211> LENGTH: 1071
<212> TYPE: DNA
<213> ORGANISM: Artificial Sequence
<220> FEATURE:
<223> OTHER INFORMATION: Synthetic polynucleotide

<400> SEQUENCE: 2

```
atggcagccg aacagcagt tggagcctgg gtgctggtcc tcagtctgtg gggggcagta      60
gtaggtgctg aattcatggc tagcatgact ggtggacagc aaatgggtac tggatctgct    120
caaaacatca cagcccggat tggcgagcca ctggtgctga agtgtaaggg ggccccccaag   180
aaaccacccc agcggctgga atggaaactg aacacaggcc ggacagaagc ttggaaggtc    240
ctgtctcccc agggaggagg ccctgggac agtgtggctc gtgtccttcc caacggctcc    300
ctcttccttc cggctgtcgg gatccaggat gaggggattt ccggtgcca ggcaatgaac     360
aggaatggaa aggagaccaa gtccaactac cgagtccgtg tctaccagat tcctgggaag   420
ccagaaattg tagattctgc ctctgaactc acggctggtg ttcccaataa ggtggggaca    480
tgtgtgtcag agggaagcta ccctgcaggg actcttagct ggcacttgga tgggaagccc    540
ctggtgccta atgagaaggg agtatctgtg aaggaacaga ccaggagaca ccctgagaca    600
gggctcttca cactgcagtc ggagctaatg gtgacccag cccggggagg agatccccgt    660
cccaccttct cctgtagctt cagcccaggc cttccccgac accgggcctt gcgcacagcc    720
cccatccagc ccgtgtctg ggagcctgtg cctctggagg aggtccaatt ggtggtggag    780
ccagaaggtg gagcagtagc tcctggtgga accgtaaccc tgacctgtga agtccctgcc    840
cagccctctc ctcaaaatcca ctggatgaag gatggtgtgc ccttgcccct tccccccagc    900
cctgtgctga tcctccctga gataggggcct caggaccagg gaacctacag ctgtgtggcc    960
acccattcca gccacgggcc ccaggaaagc cgtgctgtca gcatcagcat catcgaacca   1020
ggcgaggagg ggccaactgc aggctctgtg gaggatcag ggctgggaac t             1071
```

<210> SEQ ID NO 3
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 3

Met Ala Ser Met Thr Gly Gly Gln Gln Met Gly Thr
1               5                   10

<210> SEQ ID NO 4
<211> LENGTH: 332
<212> TYPE: PRT
<213> ORGANISM: Artificial Sequence
<220> FEATURE:
<223> OTHER INFORMATION: Synthetic polypeptide

<400> SEQUENCE: 4

Met Ala Ser Met Thr Gly Gly Gln Gln Met Gly Thr Gly Ser Ala Gln
1               5                   10                  15

Asn Ile Thr Ala Arg Ile Gly Glu Pro Leu Val Leu Lys Cys Lys Gly
                20                  25                  30

Ala Pro Lys Lys Pro Pro Gln Arg Leu Glu Trp Lys Leu Asn Thr Gly
            35                  40                  45

Arg Thr Glu Ala Trp Lys Val Leu Ser Pro Gln Gly Gly Gly Pro Trp
        50                  55                  60

Asp Ser Val Ala Arg Val Leu Pro Asn Gly Ser Leu Phe Leu Pro Ala
65                  70                  75                  80

Val Gly Ile Gln Asp Glu Gly Ile Phe Arg Cys Gln Ala Met Asn Arg
                85                  90                  95

Asn Gly Lys Glu Thr Lys Ser Asn Tyr Arg Val Arg Val Tyr Gln Ile
                100                 105                 110

Pro Gly Lys Pro Glu Ile Val Asp Ser Ala Ser Glu Leu Thr Ala Gly
            115                 120                 125

Val Pro Asn Lys Val Gly Thr Cys Val Ser Glu Gly Ser Tyr Pro Ala
130                 135                 140

Gly Thr Leu Ser Trp His Leu Asp Gly Lys Pro Leu Val Pro Asn Glu
145                 150                 155                 160

Lys Gly Val Ser Val Lys Glu Gln Thr Arg Arg His Pro Glu Thr Gly
                165                 170                 175

Leu Phe Thr Leu Gln Ser Glu Leu Met Val Thr Pro Ala Arg Gly Gly
            180                 185                 190

Asp Pro Arg Pro Thr Phe Ser Cys Ser Phe Ser Pro Gly Leu Pro Arg
        195                 200                 205

His Arg Ala Leu Arg Thr Ala Pro Ile Gln Pro Arg Val Trp Glu Pro
    210                 215                 220

Val Pro Leu Glu Glu Val Gln Leu Val Val Glu Pro Glu Gly Gly Ala
225                 230                 235                 240

Val Ala Pro Gly Gly Thr Val Thr Leu Thr Cys Glu Val Pro Ala Gln
                245                 250                 255

Pro Ser Pro Gln Ile His Trp Met Lys Asp Gly Val Pro Leu Pro Leu
            260                 265                 270

Pro Pro Ser Pro Val Leu Ile Leu Pro Glu Ile Gly Pro Gln Asp Gln
        275                 280                 285

Gly Thr Tyr Ser Cys Val Ala Thr His Ser Ser His Gly Pro Gln Glu
    290                 295                 300

Ser Arg Ala Val Ser Ile Ser Ile Ile Glu Pro Gly Glu Glu Gly Pro
305                 310                 315                 320

Thr Ala Gly Ser Val Gly Gly Ser Gly Leu Gly Thr

```
                   325                 330
```

<210> SEQ ID NO 5
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 5
gaagatctgc tcaaaccatc acagcccgga ttggc                           35

<210> SEQ ID NO 6
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 6
gggaaggaca cgagccac                                              18

<210> SEQ ID NO 7
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 7
accggctccc tcttccttcc g                                          21

<210> SEQ ID NO 8
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 8
gctctagatc aagttcccag ccctg                                      25

<210> SEQ ID NO 9
<211> LENGTH: 1035
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(1035)

<400> SEQUENCE: 9

```
atg gct agc atg act ggt gga cag caa atg ggt act ctg gtg ccc cgg        48
Met Ala Ser Met Thr Gly Gly Gln Gln Met Gly Thr Leu Val Pro Arg
1               5                   10                  15 gga tct ggc gac gga tct ggc ggc ggc agc ggc ggc caa aac atc aca        96
Gly Ser Gly Asp Gly Ser Gly Gly Gly Ser Gly Gly Gln Asn Ile Thr
            20                  25                  30 gcc cgg att ggc gag cca ctg gtg ctg aag tgt aag ggg gcc ccc aag       144
Ala Arg Ile Gly Glu Pro Leu Val Leu Lys Cys Lys Gly Ala Pro Lys
        35                  40                  45 aaa cca ccc cag cgg ctg gaa tgg aaa ctg aac aca ggc cgg aca gaa       192
Lys Pro Pro Gln Arg Leu Glu Trp Lys Leu Asn Thr Gly Arg Thr Glu
    50                  55                  60
```

```
gct tgg aag gtc ctg tct ccc cag gga gga ggc ccc tgg gac agt gtg    240
Ala Trp Lys Val Leu Ser Pro Gln Gly Gly Gly Pro Trp Asp Ser Val
 65                  70                  75                  80 gct cgt gtc ctt ccc aac ggc tcc ctc ttc ctt ccg gct gtc ggg atc    288
Ala Arg Val Leu Pro Asn Gly Ser Leu Phe Leu Pro Ala Val Gly Ile
                 85                  90                  95 cag gat gag ggg att ttc cgg tgc cag gca atg aac agg aat gga aag    336
Gln Asp Glu Gly Ile Phe Arg Cys Gln Ala Met Asn Arg Asn Gly Lys
            100                 105                 110 gag acc aag tcc aac tac cga gtc cgt gtc tac cag att cct ggg aag    384
Glu Thr Lys Ser Asn Tyr Arg Val Arg Val Tyr Gln Ile Pro Gly Lys
        115                 120                 125 cca gaa att gta gat tct gcc tct gaa ctc acg gct ggt gtt ccc aat    432
Pro Glu Ile Val Asp Ser Ala Ser Glu Leu Thr Ala Gly Val Pro Asn
    130                 135                 140 aag gtg ggg aca tgt gtg tca gag gga agc tac cct gca ggg act ctt    480
Lys Val Gly Thr Cys Val Ser Glu Gly Ser Tyr Pro Ala Gly Thr Leu
145                 150                 155                 160 agc tgg cac ttg gat ggg aag ccc ctg gtg cct aat gag aag gga gta    528
Ser Trp His Leu Asp Gly Lys Pro Leu Val Pro Asn Glu Lys Gly Val
                165                 170                 175 tct gtg aag gaa cag acc agg aga cac cct gag aca ggg ctc ttc aca    576
Ser Val Lys Glu Gln Thr Arg Arg His Pro Glu Thr Gly Leu Phe Thr
            180                 185                 190 ctg cag tcg gag cta atg gtg acc cca gcc cgg gga gga gat ccc cgt    624
Leu Gln Ser Glu Leu Met Val Thr Pro Ala Arg Gly Gly Asp Pro Arg
        195                 200                 205 ccc acc ttc tcc tgt agc ttc agc cca ggc ctt ccc cga cac cgg gcc    672
Pro Thr Phe Ser Cys Ser Phe Ser Pro Gly Leu Pro Arg His Arg Ala
    210                 215                 220 ttg cgc aca gcc ccc atc cag ccc cgt gtc tgg gag cct gtg cct ctg    720
Leu Arg Thr Ala Pro Ile Gln Pro Arg Val Trp Glu Pro Val Pro Leu
225                 230                 235                 240 gag gag gtc caa ttg gtg gtg gag cca gaa ggt gga gca gta gct cct    768
Glu Glu Val Gln Leu Val Val Glu Pro Glu Gly Gly Ala Val Ala Pro
                245                 250                 255 ggt gga acc gta acc ctg acc tgt gaa gtc cct gcc cag ccc tct cct    816
Gly Gly Thr Val Thr Leu Thr Cys Glu Val Pro Ala Gln Pro Ser Pro
            260                 265                 270 caa atc cac tgg atg aag gat ggt gtg ccc ttg ccc ctt ccc ccc agc    864
Gln Ile His Trp Met Lys Asp Gly Val Pro Leu Pro Leu Pro Pro Ser
        275                 280                 285 cct gtg ctg atc ctc cct gag ata ggg cct cag gac cag gga acc tac    912
Pro Val Leu Ile Leu Pro Glu Ile Gly Pro Gln Asp Gln Gly Thr Tyr
    290                 295                 300 agc tgt gtg gcc acc cat tcc agc cac ggg ccc cag gaa agc cgt gct    960
Ser Cys Val Ala Thr His Ser Ser His Gly Pro Gln Glu Ser Arg Ala
305                 310                 315                 320 gtc agc atc agc atc atc gaa cca ggc gag gag ggg cca act gca ggc   1008
Val Ser Ile Ser Ile Ile Glu Pro Gly Glu Glu Gly Pro Thr Ala Gly
                325                 330                 335 tct gtg gga gga tca ggg ctg gga act                                1035
Ser Val Gly Gly Ser Gly Leu Gly Thr
            340                 345

<210> SEQ ID NO 10
<211> LENGTH: 345
<212> TYPE: PRT
<213> ORGANISM: Artificial Sequence
<220> FEATURE:
<223> OTHER INFORMATION: Synthetic Construct
```

<400> SEQUENCE: 10

```
Met Ala Ser Met Thr Gly Gly Gln Gln Met Gly Thr Leu Val Pro Arg
1               5                   10                  15

Gly Ser Gly Asp Gly Ser Gly Gly Ser Gly Gly Gln Asn Ile Thr
            20                  25                  30

Ala Arg Ile Gly Glu Pro Leu Val Leu Lys Cys Lys Gly Ala Pro Lys
            35                  40                  45

Lys Pro Pro Gln Arg Leu Glu Trp Lys Leu Asn Thr Gly Arg Thr Glu
50                      55                  60

Ala Trp Lys Val Leu Ser Pro Gln Gly Gly Pro Trp Asp Ser Val
65                  70                  75                  80

Ala Arg Val Leu Pro Asn Gly Ser Leu Phe Leu Pro Ala Val Gly Ile
                85                  90                  95

Gln Asp Glu Gly Ile Phe Arg Cys Gln Ala Met Asn Arg Asn Gly Lys
            100                 105                 110

Glu Thr Lys Ser Asn Tyr Arg Val Arg Val Tyr Gln Ile Pro Gly Lys
            115                 120                 125

Pro Glu Ile Val Asp Ser Ala Ser Glu Leu Thr Ala Gly Val Pro Asn
130                     135                 140

Lys Val Gly Thr Cys Val Ser Glu Gly Ser Tyr Pro Ala Gly Thr Leu
145                 150                 155                 160

Ser Trp His Leu Asp Gly Lys Pro Leu Val Pro Asn Glu Lys Gly Val
                165                 170                 175

Ser Val Lys Glu Gln Thr Arg Arg His Pro Glu Thr Gly Leu Phe Thr
            180                 185                 190

Leu Gln Ser Glu Leu Met Val Thr Pro Ala Arg Gly Gly Asp Pro Arg
        195                 200                 205

Pro Thr Phe Ser Cys Ser Phe Ser Pro Gly Leu Pro Arg His Arg Ala
210                 215                 220

Leu Arg Thr Ala Pro Ile Gln Pro Arg Val Trp Glu Pro Val Pro Leu
225                 230                 235                 240

Glu Glu Val Gln Leu Val Val Glu Pro Glu Gly Gly Ala Val Ala Pro
                245                 250                 255

Gly Gly Thr Val Thr Leu Thr Cys Glu Val Pro Ala Gln Pro Ser Pro
            260                 265                 270

Gln Ile His Trp Met Lys Asp Gly Val Pro Leu Pro Leu Pro Pro Ser
        275                 280                 285

Pro Val Leu Ile Leu Pro Glu Ile Gly Pro Gln Asp Gln Gly Thr Tyr
    290                 295                 300

Ser Cys Val Ala Thr His Ser Ser His Gly Pro Gln Glu Ser Arg Ala
305                 310                 315                 320

Val Ser Ile Ser Ile Ile Glu Pro Gly Glu Glu Gly Pro Thr Ala Gly
                325                 330                 335

Ser Val Gly Gly Ser Gly Leu Gly Thr
            340                 345
```

<210> SEQ ID NO 11
<211> LENGTH: 329
<212> TYPE: PRT
<213> ORGANISM: Artificial Sequence
<220> FEATURE:
<223> OTHER INFORMATION: Synthetic polypeptide

<400> SEQUENCE: 11

```
Gly Ser Gly Asp Gly Ser Gly Gly Ser Gly Gly Gln Asn Ile Thr
 1               5                  10                  15

Ala Arg Ile Gly Glu Pro Leu Val Leu Lys Cys Lys Gly Ala Pro Lys
            20                  25                  30

Lys Pro Pro Gln Arg Leu Glu Trp Lys Leu Asn Thr Gly Arg Thr Glu
        35                  40                  45

Ala Trp Lys Val Leu Ser Pro Gln Gly Gly Gly Pro Trp Asp Ser Val
 50                  55                  60

Ala Arg Val Leu Pro Asn Gly Ser Leu Phe Leu Pro Ala Val Gly Ile
 65                  70                  75                  80

Gln Asp Glu Gly Ile Phe Arg Cys Gln Ala Met Asn Arg Asn Gly Lys
                85                  90                  95

Glu Thr Lys Ser Asn Tyr Arg Val Arg Val Tyr Gln Ile Pro Gly Lys
            100                 105                 110

Pro Glu Ile Val Asp Ser Ala Ser Glu Leu Thr Ala Gly Val Pro Asn
        115                 120                 125

Lys Val Gly Thr Cys Val Ser Glu Gly Ser Tyr Pro Ala Gly Thr Leu
130                 135                 140

Ser Trp His Leu Asp Gly Lys Pro Leu Val Pro Asn Glu Lys Gly Val
145                 150                 155                 160

Ser Val Lys Glu Gln Thr Arg Arg His Pro Glu Thr Gly Leu Phe Thr
                165                 170                 175

Leu Gln Ser Glu Leu Met Val Thr Pro Ala Arg Gly Gly Asp Pro Arg
            180                 185                 190

Pro Thr Phe Ser Cys Ser Phe Ser Pro Gly Leu Pro Arg His Arg Ala
        195                 200                 205

Leu Arg Thr Ala Pro Ile Gln Pro Arg Val Trp Glu Pro Val Pro Leu
210                 215                 220

Glu Glu Val Gln Leu Val Val Glu Pro Glu Gly Gly Ala Val Ala Pro
225                 230                 235                 240

Gly Gly Thr Val Thr Leu Thr Cys Glu Val Pro Ala Gln Pro Ser Pro
                245                 250                 255

Gln Ile His Trp Met Lys Asp Gly Val Pro Leu Pro Leu Pro Pro Ser
            260                 265                 270

Pro Val Leu Ile Leu Pro Glu Ile Gly Pro Gln Asp Gln Gly Thr Tyr
        275                 280                 285

Ser Cys Val Ala Thr His Ser Ser His Gly Pro Gln Glu Ser Arg Ala
290                 295                 300

Val Ser Ile Ser Ile Ile Glu Pro Gly Glu Glu Gly Pro Thr Ala Gly
305                 310                 315                 320

Ser Val Gly Gly Ser Gly Leu Gly Thr
                325

<210> SEQ ID NO 12
<211> LENGTH: 1065
<212> TYPE: DNA
<213> ORGANISM: Artificial Sequence
<220> FEATURE:
<223> OTHER INFORMATION: Synthetic polynucleotide

<400> SEQUENCE: 12
atggctgctg gcaccgctgt gggagcttgg gtgctggtgc tgtccctgtg gggcgctgtc      60
gtgggcgccg agttcatggc ctctatgacc ggcggacagc agatgggcac ccagaacatc     120
accgcccgga tcggagagcc cctggtcctg aagtgcaagg gcgctcccaa gaagcccccc     180
```

```
cagcggctgg aatggaagct gaacaccggc cggaccgagg cctggaaggt gctgagtcct    240
cagggcggag gcccttggga ctccgtggcc agagtgctgc ccaacggctc cctgtttctg    300
cccgccgtgg gcatccagga cgagggcatc ttcaggtgtc aggccatgaa ccggaacggc    360
aaagagacaa agtccaacta cagagtgcgg gtgtaccaga tccccggcaa gcccgagatc    420
gtggactccg cctctgagct gaccgctggc gtgcccaaca aagtgggcac ctgtgtgtcc    480
gagggctcct accctgccgg caccctgtct tggcacctgg acggcaagcc tctggtgccc    540
aacgagaagg gcgtgtccgt gaaagagcag accagacggc accccgagac aggcctgttc    600
accctgcagt ccgagctgat ggtcaccccc gccagaggcg gcgacccag acctaccttc    660 agctgctcct tctcccctgg cctgccccgg cacagagccc tgagaaccgc ccccatccag    720
cccagagtgt gggagcccgt gcccctggaa gaggtgcagc tggtggtgga acctgagggc    780
ggagctgtgg ctcctggcgg caccgtgacc ctgacctgtg aagtgcctgc ccagcccagc    840
ccccagatcc actggatgaa ggacggcgtg cccctgcccc tgcctccctc tcctgtgctg    900
atcctgcctg agatcggccc ccaggaccag ggcacctact cttgcgtggc cacccactcc    960
tcccacggcc ctcaggaatc tcgggccgtc agcatctcca tcatcgagcc cggcgaggaa   1020
ggccctaccg ctggctctgt gggcggctct ggcctgggca cctga                    1065
```